(12) United States Patent
Raines et al.

(10) Patent No.: US 8,722,878 B2
(45) Date of Patent: May 13, 2014

(54) BIOMASS HYDROLYSIS

(75) Inventors: Ronald T. Raines, Madison, WI (US); Joseph B. Binder, Berkeley, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 525 days.

(21) Appl. No.: 12/822,693

(22) Filed: Jun. 24, 2010

(65) Prior Publication Data

US 2011/0065159 A1 Mar. 17, 2011

Related U.S. Application Data

(60) Provisional application No. 61/222,397, filed on Jul. 1, 2009.

(51) Int. Cl.
*C07H 1/00* (2006.01)
*C07H 3/00* (2006.01)
*C08B 37/00* (2006.01)

(52) U.S. Cl.
USPC .......................................................... 536/124

(58) Field of Classification Search
None
See application file for complete search history.

(56) References Cited

U.S. PATENT DOCUMENTS

| | | | |
|---|---|---|---|
| 2,223,714 A | 12/1940 | Bates et al. | |
| 2,750,394 A | 6/1956 | Peniston | |
| 2,917,520 A | 12/1959 | Cope | |
| 2,929,823 A | 3/1960 | Garber et al. | |
| 3,007,941 A | 11/1961 | Copelin et al. | |
| 3,118,912 A | 1/1964 | Smith | |
| 3,257,417 A | 6/1966 | Dunlop et al. | |
| 4,018,620 A | 4/1977 | Penque | |
| 4,154,744 A | 5/1979 | Hamada et al. | |
| 4,278,790 A | 7/1981 | McCormick | |
| 4,339,387 A | 7/1982 | Fleche et al. | |
| 4,452,640 A | 6/1984 | Chen et al. | |
| 4,520,105 A | 5/1985 | Sinner | |
| 4,740,605 A | 4/1988 | Rapp | |
| 4,764,627 A | 8/1988 | Diebold et al. | |
| 4,780,552 A | 10/1988 | Wambach et al. | |
| 4,787,939 A | 11/1988 | Barker et al. | |
| 4,897,497 A | 1/1990 | Fitzpatrick | |
| 4,971,657 A | 11/1990 | Avignon et al. | |
| 5,347,018 A | 9/1994 | Clark, Jr. et al. | |
| 5,562,777 A | 10/1996 | Farone et al. | |
| 5,597,714 A | 1/1997 | Farone et al. | |
| 5,726,046 A | 3/1998 | Farone et al. | |
| 6,423,145 B1 | 7/2002 | Nguyen et al. | |
| 6,603,026 B2 | 8/2003 | Lightner | |
| 7,572,925 B2 | 8/2009 | Dumesic et al. | |
| 7,880,049 B2 | 2/2011 | Dumesic et al. | |
| 2007/0215300 A1 | 9/2007 | Upfal et al. | |
| 2008/0033187 A1 | 2/2008 | Zhao et al. | |
| 2008/0033188 A1 | 2/2008 | Dumesic et al. | |
| 2008/0185112 A1 | 8/2008 | Argyropoulos | |
| 2008/0190013 A1 | 8/2008 | Argyropoulos | |
| 2008/0227162 A1 | 9/2008 | Varanasi et al. | |
| 2009/0020112 A1 | 1/2009 | Massonne et al. | |
| 2009/0062524 A1 | 3/2009 | Massonne et al. | |
| 2009/0084509 A1 | 4/2009 | Luo et al. | |
| 2009/0088564 A1 | 4/2009 | Luo et al. | |
| 2009/0124839 A1 | 5/2009 | Dumesic et al. | |
| 2009/0198046 A1 | 8/2009 | Fanselow et al. | |
| 2009/0242414 A1 | 10/2009 | Welz-Biermann et al. | |
| 2009/0255171 A1 | 10/2009 | Dumesic et al. | |
| 2010/0004437 A1 | 1/2010 | Binder et al. | |
| 2010/0324310 A1 | 12/2010 | Dumesic et al. | |
| 2011/0180062 A1 | 7/2011 | Takeshima et al. | |
| 2013/0158254 A1 | 6/2013 | Binder et al. | |

FOREIGN PATENT DOCUMENTS

| | | |
|---|---|---|
| CN | 101289817 | 10/2008 |
| EP | 1 860 201 | 11/2007 |
| FR | 2663933 A1 | 1/1992 |
| FR | 2664273 A1 | 1/1992 |
| FR | 2669635 A1 | 5/1992 |
| GB | 591858 | 9/1947 |
| GB | 600871 | 4/1948 |
| GB | 876463 | 9/1961 |
| GR | 860020 | 5/1986 |
| JP | S61-205489 A | 9/1986 |
| JP | S62-111700 A | 5/1987 |
| JP | 2005232116 | 9/2005 |
| JP | 2006223152 A | 8/2006 |
| JP | 2009001733 A | 1/2009 |

(Continued)

OTHER PUBLICATIONS

Wyman et al. Hydrolysis of cellulose and hemicellulose, in Polysaccharides: Structural Diversity and Functional Versatility, ed. Dumitriu. Marcel Dekker Inc., New York, 2nd edn., 2005, pp. 995-1033.*
Amarasekara et al. (Web Release Oct. 2009) "Hydrolysis and Decomposition of Cellulose in Brönsted Ionic Liquids Under Mild Conditions," *Ind. Eng. Chem. Res.* 48:10152-10155.
Atsumi et al. (Jan. 2008) "Non-Fermentative Pathways for Synthesis of Branched-Chain Higher Alcohols as Biofuels," *Nature* 451:86-89.
Benvenuti et al. (2000) "Heterogenous Zirconium and Titanium Catalysts for the Selective Synthesis of 5-Hydroxymethyl-2-Furaldehyde from Carbohydrates," *Appl. Catal. A. Gen.* 193:147-153.
Bicker et al. (Web Release Feb. 2003) "Dehydration of Fructose to 5-Hydroxymethylfurfural in Sub- and Supercritical Acetone," *Green Chem.* 5:280-284.

(Continued)

*Primary Examiner* — Layla Bland
(74) *Attorney, Agent, or Firm* — Lathrop & Gage LLP

(57) ABSTRACT

High-yielding method for chemical hydrolysis of lignocellulose into monosaccharides. The process of the invention can additionally be applied to cellulose, xylan and related biomass polysaccharides, such as galactan, mannan, or arabinan. The method is employed for hydrolysis of a biomass polysaccharide substrate. The process is carried out in an ionic liquid in which cellulose is soluble in the presence of catalytic acid at a temperature sufficiently high to initiate hydrolysis. Water is added to the reaction mixture after initiation of hydrolysis at a rate controlled to avoid precipitation yet avoid undesired sugar dehydration products such ad HMF. Hydrolysis product is useful as feedstock for fermentations including fermentation processes for ethanol, butanol and other fuels.

17 Claims, 5 Drawing Sheets

(56) References Cited

FOREIGN PATENT DOCUMENTS

| | | |
|---|---|---|
| JP | 2009001734 A | 1/2009 |
| JP | 2009060828 A | 3/2009 |
| WO | WO 92/10486 | 6/1992 |
| WO | WO 03/029329 | 4/2003 |
| WO | WO 2005/017001 | 2/2005 |
| WO | WO 2005/018799 | 3/2005 |
| WO | WO2007101811 | 9/2007 |
| WO | WO 2007/112090 | 10/2007 |
| WO | WO 2007/138256 | 12/2007 |
| WO | WO 2007/146636 | 12/2007 |
| WO | WO2008090155 | 7/2008 |
| WO | WO 2008/098032 | 8/2008 |
| WO | WO 2008/098036 | 8/2008 |
| WO | WO 2008/112291 | 9/2008 |
| WO | WO 2008/119770 | 10/2008 |
| WO | WO 2009/024607 | 2/2009 |
| WO | WO 2009/030512 | 3/2009 |
| WO | WO 2009/030949 | 3/2009 |
| WO | WO 2009/030950 | 3/2009 |
| WO | WO 2009/047023 | 4/2009 |
| WO | WO 2009/155297 | 12/2009 |
| WO | WO 2012/064701 | 5/2012 |

OTHER PUBLICATIONS

Binder et al. (Mar. 2010) "Fermentable Sugars by Chemical Hydrolysis of Biomass," *Proc. Nat. Acad. Sci. USA* 107(10):4516-4521.

Binder J.B. et al. (Sep. 2009) "Reactions of lignin model compounds in ionic liquids," *Biomass and Bioenergy* 33(9):1122-11303.

Binder et al. (Jan. 2009) "Simple Chemical Transformation of Lignocellulosic Biomass into Furans for Fuels and Chemicals," *J. Amer. Chem. Soc.* 131:1979-1985, published on web Jan. 21, 2009.

Blazej et al. (1985) "Degradation reactions of cellulose and lignocellulose," In; *Cellulose and its Derivatives: Chemistry, Biochemistry, and Applications*, Kennedy, J. F., Phillips, G. O., Wedlock, D. J., Williams, P. A., Eds.; Ellis Horwood Ltd.: Chichester, England, 1985; pp. 97-117.

Brown et al. (1982) "Dehydration Reactions of Fructose in Non-Aqueous Media," *J. Chem. Technol. Biotechnol.* 32:920-924.

Cao et al. (1995) "Acid hydrolysis of cellulose in zinc chloride solution," *Appl. Biochem. Biotechnol.* 51:21-28.

Carlini et al. (2004) "Selective Saccharides Dehydration to 5-Hydroxymethyl-2-Furaldehyde by Heterogenous Niobium Catalysts," *Appl. Catal. A Gen.* 183:295-302.

Chheda et al. (Web Release Jan. 2007) "Production of 5-Hydroxymethylfurfural and furfural by dehydration of Biomass-Derived Mono- and Poly-Saccharides," *Green Chem.* 9:342-350, published on web Jan. 17, 2007.

Chheda et al. (Sep. 2007) "Liquid-phase catalytic processing of biomass-derived oxygenated hydrocarbons to fuels and chemicals," *Angew. Chem. Int. Ed.* 46:7164-7183.

Chheda et al. (Web Release Jan. 2007) "An Overview of Dehydration, Aldol Condensation and Hydrogenation Processes for Production of Liquid Alkanes from Biomass Derived Carbohydrates," *Catal. Today* 123:59-70.

Chiappe et al. (Web Release Sep. 2004) "Ionic liquids; solvent properties and organic reactivity," *Phys. Org. Chem.*, 18:275-297, published online Sep. 21, 2004.

Chowdhury et al. (Mar. 2007) "Reactivity of Ionic Liquids," *Tetrahedron* 63:2363-2389, available online Dec. 8, 2006.

Christensen et al. (Mar. 2008) "The Renewable Chemicals Industry," *ChemSusChem* 1:283-289.

Dadgar et al. (1983) "The Production of Hydromethyl Furfural from Sawdust," *Biotechnol. Bioeng. Symp.* 13:41-52.

Dias et al. (Apr. 2005) "Dehydration of Xylose into Furfural Over Micro-Mesoporous Sulfonic Acid Catalysts," *J. Catalysis* 229:414-423.

Dunning et al. (1945) "The Saccharification of Agricultural Residues: A Continuous Process," *Ind. Eng. Chem.* 37:24-29.

Ebner et al. (Oct. 2008) "Side reaction of cellulose with common 1-alkyl-3-methylimidazolium-based ionic liquids," *Tetrahedron Lett.* 49:7322-7324, available online Oct. 17, 2008.

El Seoud et al. (Sep. 2007) "Applications of ionic liquids in carbohydrate chemistry: A window of opportunities," *Biomacromolecules* 8:2629-2647.

Farina et al. (1988) "Fuel Alcohol Production from Agricultural Lignocellulosic Feedstocks," *Energy Sources* 10:231-237.

Fischer, H. Leipner, K. Thummler, E. Brendler, J. Peters (2003) "Inorganic molten salts as solvents for cellulose," Cellulose 10, 227-236.

Fort et al. (May 2007) "Can Ionic Liquids Dissolve Wood? Processing and Analysis of Lignocellulosic Materials with 1-n-butyl-3-methylimidazolium Chloride," *Green Chem.* 9:63-69, published on web Oct. 17, 2006.

Fortman et al. (May 2008) "Biofuel Alternatives to Ethanol: Pumping the Microbial Well," *Trends Biotechnol.* 26:375-381.

Girisuta et al. (Web Release Feb. 2007) "Kinetic Study on the Acid Catalyzed Hydrolysis of Cellulose to Levulinic Acid," *Ind. Eng. Chem. Res.* 46(6):1696-1708.

Hermanutz et al. (Dec. 2006) "New developments in the manufacture of cellulose fibers with ionic liquids," *Chem. Fibers Int.* 6:342-343.

Himmel et al. (Feb. 2007) "Biomass recalcitrance: Engineering Plants and Enzymes for Biofuels Production," *Science* 315:804-807.

Huber et al. (Jun. 3, 2005) "Production of Liquid Alkanes by Aqueous-Phase Processing of Biomass-Derived Carbohydrates," *Science* 308:1446-1450.

International Search Report and Written Opinion, Corresponding to International Application No. PCT/US10/39812, mailed Aug. 20, 2010.

International Preliminary Report on Patentability, Corresponding to PCT/US2010/039812, issued Jan. 4, 2012.

Kumar et al. (Web Release Mar. 2009) "Methods for Pretreatment of Lignocellulosic Biomass for Efficient Hydrolysis and Biofuel Production," *Indus Eng. Chem. Res.* 48:3713-3729.

Kunkes et al. (Oct. 2008) "Catalytic conversion of biomass to monofunctional hydrocarbons and targeted liquid-fuel classes," *Science* 322:417-421.

Lansalot-Matras et al. (Web Release Sep. 2003) "Dehydration of fructose into 5-hydroxymethylfurfural in the presence of ionic liquids," *Catal. Commun.* 4:517-520.

Lange et al. (Web Release Jul. 2007) "Lignocellulose conversion: An introduction to chemistry, process and economics," *Biofuels Bioprod. Bioref.* 1:39-48, published online Jul. 18, 2007.

Li et al. (Aug. 2007) "Efficient acid-catalyzed hydrolysis of cellulose in ionic liquid," *Adv. Synth. Catal.* 349:1847-1850.

Li et al. (Web Release Dec. 2008) "Acid in ionic liquid: An efficient system for hydrolysis of lignocellulose," *Green Chem.* 10:177-182, published on web Dec. 17, 2007.

Lora et al. (2002) "Recent Industrial Applications of Lignin: A Sustainable Alternative to Nonrenewable Materials," *J. Polym. Environ.* 10:39-48.

Marzialetti et al. (Aug. 2008) "Dilute acid hydrolysis of loblolly pine: a comprehensive approach," Ind. Eng. Chem. Res. 47:7131-7140, published on web Aug. 26, 2008.

Mascal et al. (Sep. 2008) "Direct, High-Yield Conversion of Cellulose into Biofuel," *Angew. Chem. Int. Ed.* 47:7924-7926.

McCormick (Dec. 1985) "Solution Studies of Cellulose in Lithium Chloride and N,N-Dimethylacetamide," *Macromolecules* 18(12):2394-2401.

Mosier et al. (Web Release Sep. 2004) "Features of Promising Technologies for Pretreatment of Lignocellulosic Biomass," *Bioresour. Technol.* 96:673-686.

Osada et al. (Web Release Dec. 2004) "Low Temperature Catalytic Gasification of Lignin and cellulose with a Ruthenium Catalyst in Supercritical Water," 18, 327-333, published on web Dec. 5, 2003.

Potthast et al. (Mar. 2002) "The Cellulose Solvent System N,N-dimethylacetamide/Lithium Chloride Revisited: The Effect of Water on Physicochemical Properties and Chemical Stability," *Cellulose* 9(1):41-53.

Potthast et al. (Oct. 2002) "Degradation of Cellulosic Materials by Heating in DMAc/LiCl," *Tetrahedron Lett.* 43(43):7757-7759.

(56) References Cited

OTHER PUBLICATIONS

Potthast et al. (Jan. 2003) "Hydrolytic Processes and Condensation Reactions in the Cellulose Solvent System N,N-dimethylacetamide/Lithium Chloride. Part 2: Degradation of Cellulose," *Polymer* 44(1):7-17.
Pu et al. (Jan. 2007) "Ionic Liquid as a Green Solvent for Lignin," *J. Wood Chem. Technol.* 27(1):23-33.
Rinaldi et al. (Sep. 2008) "Depolymerization of cellulose using solid catalysts in ionic liquids," *Angew. Chem. Int. Ed.* 47:8047-8050.
Rivers et al. (1984) "Limitations of the DNS Assay for Reducing Sugars from Saccharified Lignocellulosics," *Biotechnol. Bioeng.* 26:800-802.
Robinson et al. (Web Release Nov. 2003) "The Use of Calalytic Hydrogenation to Intercept Carbohydrates in a Dilute Acid Hydroluusis of Biomass to Effect a Clean Separation from Lignin," *Biomass. Bioeng.* 26(5):473-483.
Sievers et al. (Web Release Jan. 2009) "Ionic-liquid—phase hydrolysis of pine wood," *Ind. Eng. Chem. Res.* 48(3):1277-1286.
Srokol et al. (Apr. 2004) "Hydrothermal upgrading of biomass to biofuel; studies on some monosaccharide model compounds," *Carbohydrate Res.* 339:1717-1726.
Swatloski et al. (Apr. 2002) "Dissolution of Celluose with Ionic Liquids," *J. Amer. Chem. Soc.* 124:4974-4975.
Szmant et al. (Jan. 1981) "The Preparation of 5-Hydroxtmethlfurfuraldehyde from High Fructose Corn Syrup and Other Carbohydrates," *J. Chem. Technol. Biotechnol.* 31:135-145.
Tsao et al. (1982) "Production of Ethanol and Chemicals from Cellulosic Materials," *Process Biochem.* :34-38.
Tyrlik et al. (Apr. 1996) "Concentrated Water Solutions of Salts as Solvents for Reaction of Carbohydrates. Part 2. Influence of Some Magnesium Salts and Some Ruthenium Species on Catalysts of Dehydration of Glucose," *J. Mol. Catal. A. Chem.* 106(3):223-233.
Van Dam et al. (Mar. 1986) "The Conversion of Fructose and Glucose in Acidic Media: Formation of Hydroxymethylfurfural," *Starch* 38:95-101.
Van Haveren et al. (Jan. 2008) Bulk chemicals from biomass. *Biofuels Bioprod. Bioref.* 2:41-57, published on line Dec. 19, 2007.
Vanoye et al. (Jan. 2009) "Kinetic model for the hydrolysis of lignocellulosic biomass in the ionic liquid, 1-ethyl-3-methyl-imidazolium chloride," *Green Chem.* 11:390-396.
Vitz et al. (Jan. 2009) "Extended dissolution studies of cellulose in imidazolium based ionic liquids," *Green Chem.* 11:417-424.
Wang et al. (Oct. 2010) "The application of ionic liquids in dissolution and separation of lignocellulose" In Clean Energy Systems and Experiences (ed. K. Eguchi), Sciyo.com (www.sciyo.com), India, publisher, Chapter 4, pp. 71-84; available on-line at <http://cdn.intechopen.com/pdfs/11933/InTech-The_application_of_ionic_liquids_in_dissolution_and_separation_of_lignocellulose.pdf>.
Wyman et al. (Feb. 2005) "Comparative Sugar Recovery Data from Laboratory Scale Application of Leading Pretreatment Ttechnologies to Corn Stover," *Bioresour. Technol.* 96:2026-2032.
Xiang et al. (Mar. 2003) "Heterogeneous Aspects of Acid Hydrolysis of α-Cellulose," *Appl. Biochem. Biotechnol.* 105:505-514.
Zhang et al. (Mar. 2010) "Ionic Liquid—Water Mixtures: Enhanced Kw for Efficient Cellulosic Biomass Conversion," *Energy Fuels* 24, 2420-2417.
Zhang et al. (Jun. 2007) "Fractionating Recalcitrant Lignocellulose at Modest Reaction Conditions," *Biotechnol. Bioeng.* 97(2):214-223.
Zhao et al. (Jun. 2007) "Metal Chlorides in Ionic Liquid Solvents Convert Sugars to 5-Hydroxymethylfurfural," *Science* 316:1597-1600.
Zhu et al. (Mar. 2006) "Dissolution of cellulose with ionic liquids and its application: A mini-review," *Green Chem.* 8:325-327.
Kokorevics et al. (1997) "EGC1 Cellulose depolymerization to glucose and other water soluble polysaccharides by shear deformation and high pressure treatment", Glycoconjugate Journal 14: 669-676.
Supplementary European Search Report issued in EP 10794567 corresponding to the above-identified application on Aug. 30, 2013.

* cited by examiner

BIOMASS HYDROLYSIS

CROSS-REFERENCE TO RELATED APPLICATIONS

This application claims the benefit of U.S. provisional application 61/222,397, filed Jul. 1, 2009 which application is incorporated by reference in its entirety herein.

STATEMENT REGARDING FEDERALLY SPONSORED RESEARCH OR DEVELOPMENT

This invention was made with United States government support awarded by the following agencies: DOE DE-FC02-07ER64494. The United States government has certain rights in this invention.

BACKGROUND OF THE INVENTION

Abundant plant biomass could become a sustainable source of fuels and chemicals. Unlocking this potential requires the economical conversion of recalcitrant lignocellulose into useful intermediates, such as sugars. We report a high-yielding process for the chemical hydrolysis of lignocellulose into monosaccharides. Adding water gradually to a chloride ionic liquid containing catalytic acid leads to a nearly 90% yield of glucose from cellulose and 70-80% yield of sugars from untreated corn stover. Ion-exclusion chromatography allows recovery of the ionic liquid and delivers sugar feedstock that supports the vigorous growth of ethanologenic microbes. Hence, a simple chemical process enables crude biomass to be the sole source of carbon for a scalable biorefinery.

As the primary components of lignocellulosic biomass, the sugar polymers cellulose and hemicellulose are among the most abundant organic compounds on earth and have the potential to be renewable sources for energy and chemicals. The estimated global annual production of biomass is $1\times10^{11}$ tons, sequestering $2\times10^{21}$ J [1, 2]. For comparison, annual petroleum production amounts to $2\times10^{20}$ J, while the technically recoverable endowment of conventional crude oil is $2\times10^{22}$ J [1]. Hence, in only one decade, Earth's plants can renew in the form of cellulose, hemicellulose, and lignin all of the energy stored as conventional crude oil. The challenge for chemists is to access these polymers and convert them into fuels and chemical building blocks.

Sugars are natural intermediates in the biological and chemical conversion of lignocellulosic biomass [3-8] but access to sugars is hindered by the recalcitrance of plant cell walls [3-9]. The majority of glucose in lignocellulose is locked into highly crystalline cellulose polymers. Hemicellulose—a branched polymer of glucose, xylose, and other sugars—and lignin—a complex aromatic polymer—encase the cellulose, fortifying and protecting the plant. Deriving sugars from this heterogeneous feedstock requires both physical and chemical disruption. Enzymatic methods of saccharification are the most common, and use physical and chemical pretreatment processes[10] followed by hydrolysis with cellulases to produce sugars. The proper combination of pretreatment and enzymes for a given feedstock enables high yields of sugars from both hemicellulose and cellulose components[11]. Nonetheless, the costs of both pretreatment and enzymes (estimated to be as much as one-third of the cost of ethanol production from cellulose, [12]) and low rates of hydrolysis are potential drawbacks to enzymatic hydrolysis.

Exclusively chemical technologies for biomass hydrolysis have also been developed. As early as 1819, Braconnot demonstrated that linen dissolved in concentrated $H_2SO_4$, diluted with water, and heated was transformed into a fermentable sugar [13,14]. As in this example, concentrated acid can play a dual role in biomass hydrolysis. By disrupting its network of intra- and interchain hydrogen bonds, strong acids decrystallize cellulose and make it accessible to reagents [15] and by catalyzing the hydrolysis of glycosidic bonds, strong acids cleave cellulose and hemicellulose into sugars (FIG. 1) [3]. Bergius took advantage of these attributes of HCl in the development of a commercial process that operated in Germany from 1935 to 1948 [16, 17]. In the United States, several related processes using $H_2SO_4$ have been developed, typically with 80-90% conversion of cellulose and hemicellulose into sugars [18-22]. In a recent example, Cuzens and Farone used concentrated aqueous $H_2SO_4$ to hydrolyze agricultural residues via the Arkenol process [23], which is being commercialized by BlueFire Ethanol (Irvine, Calif., USA). In this method, biomass is decrystallized with 77% $H_2SO_4$, diluted to a water content of about 40 wt %, and hydrolyzed at 100° C. This first stage hydrolyzes nearly all of the hemicellulose and some of the cellulose. The solid residue is then subjected to a second-stage hydrolysis to release the remaining glucose. Concentrated acid hydrolysis methods produce high sugar yields, use simple catalysts, and require only short reaction times. Despite these advantages, the hazards of handling concentrated acids and the complexities of recycling them have limited the adoption of this technology.

Less hazardous and more tractable cellulose solvents would facilitate lignocellulose hydrolysis. Ionic liquids, salts with melting points near or below ambient temperature, show promise as cellulose solvents for nonwoven fiber production [24] and chemical derivatization [25,26]. Like concentrated acids, ionic liquids comprised of chloride, acetate, and other moderately basic anions disrupt the hydrogen bond network of cellulose and enable its dissolution [25-27]. Recognizing these properties, Zhao and coworkers attempted to hydrolyze cellulose in 1-butyl-3-methylimidazolium chloride ([BMIM]Cl) [28]. Using 11 wt % H2SO4 and 1.75 equiv of water relative to the glucose monomer units of the cellulose (about 1 wt % of the reaction mixture), they obtained a 43% molar yield of glucose after 9 h at 100° C. They also reported a 77% yield of total reducing sugars (TRS) based on a 3,5-dinitrosalicylic acid (DNS) assay, but did not discuss what sugars other than glucose (which is the expected cellulose hydrolysis product) comprised TRS. Zhao and coworkers also report reaction of biomass materials such as corn stover and rice straw under similar conditions, obtaining TRS yields of 66-81% but not reporting glucose yields [28]. Most likely, glucose yields from lignocellulose were no higher than those obtained with purified cellulose.

Several reports from other researchers have followed those of Zhao and coworkers. Schüth and coworkers used solid acid catalysts to depolymerize cellulose in [BMIM]Cl, obtaining mainly water-insoluble oligomers rather than glucose [30]. Recently, Jones and coworkers hydrolyzed pine wood in [BMIM]Cl under low-water conditions, obtaining molar yields of monosaccharides that were typically <20% [31]. Seddon and coworkers studied the reactivity of cellobiose in 1-ethyl-3-methylimidazolium chloride ([EMIM]Cl) and then applied their optimized conditions to pure cellulose and Miscanthus grass, obtaining 50% and 30% glucose yields, respectively [32, 33]. These low glucose yields obtained in ionic liquids reported by Zhao and co-workers contrast with the nearly quantitative yields of glucose attainable from cellulose in concentrated acids and other cellulose solvents [34].

Zhao et al. [53] and published US patent application US 2008/0033187 (published Feb. 7, 2008) report a method for conversion of a carbohydrate in an ionic liquid to produce a furan at a substantial yield. The method involves mixing carbohydrate up to the limit of solubility with the ionic liquid, and heating the carbohydrate in the presence of a catalyst at a reaction temperature and for a reaction time sufficient for conversion to furan at a substantial yield.

U.S. provisional application 61/073,285, filed Jun. 17, 2008, relates to a method for converting carbohydrate or a carbohydrate feedstock to a furan in a polar aprotic solvent in the presence of a halide salt or a mixture thereof and optionally in the presence of an acid catalyst, a metal halide catalyst or an ionic liquid (up to 40 wt %). The carbohydrate feedstock can be lignocellulosic biomass.

Published application US 2009/0062524 (published Mar. 25, 2009) relates to a process for the complete or partial degradation of cellulose by dissolving cellulose in an ionic liquid and "treating it with acid, if appropriate with addition of water." The amount of acid and water added is adjusted to achieve "complete" or "partial" degradation of cellulose. The application states "the addition of water may be necessary if the water adhering to the cellulose used is insufficient to reach the desired degree of degradation." Water is added along with acid to the solution of cellulose in the ionic liquid or the ionic liquid acid and water are premixed and the cellulose is dissolved in this mixture. The amount of water to be added is further described:

"the water content of conventional cellulose is in the range from 5 to 10% by weight, based on the total weight of the cellulose used (cellulose+adhering water). By using an excess of water and acid based on the anhydroglucose units of the cellulose, complete degradation as far as glucose is also possible. To reach partial degradation, substoichiometric amounts of water and acid are added or the reaction is stopped at that point.

The stoichiometry of the process for complete degradation of cellulose to glucose with respect to water is further discussed "(i)f . . . the cellulose which is on average made up of x anhydroglucose units is to be degraded completely to glucose, then x equivalents of water are required. Here, preference is given to using the stoichiometric amount of water ($n_{anhydroglucose\ units}/n_{acid}=1$) (sic, it is believed $n_{water}$ was intended) or an excess, preferably an excess of >3 mol % based on x." Certain examples provided in the application state that cellulose was completely degraded, but the glucose yield and the presence or absence of by-products were not reported.

Published applications WO2009030950 and WO2009030849 (both published Mar. 12, 2009) relate to processes for the preparation of water-soluble cellulose hydrolysis products in which cellulose is mixed with ionic liquids and the resulting solvate or solution is treated with an acid in the presence of water. The acid is reported to have a $pK_a$ in water of less than 2 at 25° C. The applications state that "the hydrolysis reaction requires the presence of one mole equivalent of water for each monomer unit in the cellulose. Cellulose itself contains a certain amount of water, the exact amount depending upon the source and the physical form of the cellulose, usually prepared cellulose contains at least 10-15% by weight water. However, excessively high amounts of water in the reaction mixture may result in either reduced solubility of the cellulose in the ionic liquid, and/or reduced conversion of cellulose to water-soluble hydrolysis products. Preferably the total water content of the reaction system is such that the weight ratio of water to cellulose is from 1:1 to 1:20, preferably from 1:5 to 1:15, especially about 1:10.

Patent application CN1128981, published Oct. 22, 2008, relates to a process for hydrolyzing cellulose in ionic liquid. In the method, the ionic liquid is said to be used as the solvent, and water, the equivalent weight of which is equal to or more than 1 mol, is said to be used as reactant and inorganic acids, the catalytic amount of which is the stoichiometric amount are said to be used as a catalyst. The reaction is reported to employ normal pressure and temperature between 70 to 100° C. for 2 min to 9 hr. The highest yield reported of reducing sugars was 73% with corresponding yield of glucose of 53%.

Published application WO2009047023 (published Apr. 16, 2009) relates to a process for conversion of cellulose in hydrated molten salts. Molten salts are described as those having a melting point below 200° C. and more specifically refers to hydrates of inorganic salts and hydrates of $ZnCl_2$. The method is said to be applicable to materials containing lignin and hemicellulose in addition to cellulose.

Published application US20090020112 (published Jan. 22, 2009) relates to methods for thermolysis of lignocellulosic materials which comprise combining the lignocellulosic material with ionic liquid and subjecting the mixture to pyrolytic conditions, such as heating to a temperature of about 150° C. to about 300° C., where the heating may be anaerobic, to produce a product which, for example, can be 5-hydroxymethylfurfural, furfural 2-methylfurfural, levulonic acid, levulinic acid or levoglucosensone.

Published applications WO2008112291 and US20080227162 (both published Sep. 18, 2008) relate to a method for dissolving wood, straw and other natural lignocellulosic materials in an ionic liquid under microwave irradiation and/or pressure.

While significant effort has been expended in attempts to improve the yields of desirable products from hydrolysis of lignocelluloses. There remains a significant need in the art for methods which result in high yields of monosaccharides. The present invention provides a high-yielding process for the hydrolysis of cellulose and lignocellulosic biomass which generates easily recovered sugars that are superb feedstocks for microbial growth and biocatalytic ethanol production.

SUMMARY OF THE INVENTION

The present invention provides a high-yielding method for chemical hydrolysis of lignocellulose into monosaccharides. The process can also be applied to cellulose and xylan and related biomass polysaccharides, such as galactan, mannan, or arabinan. More generally, the method is employed for hydrolysis of a biomass polysaccharide substrate. The process is carried out in an ionic liquid in which cellulose is soluble. Catalytic acid is added to polysaccharide and lignocellulose or mixtures thereof in certain ionic liquids and the mixture is heated to a temperature sufficiently high to initiate hydrolysis. The reaction is typically conducted at ambient pressure and temperatures ranging from about 70 to 140° C. and preferably 85 to 115° C. In a specific embodiment, the reaction is carried out at 100-110° C.

Concentrated acid catalyst is not required in this process to achieve high yields. The amount of acid catalyst added is between about 5-40 weight %, and preferably between 10-25 weight %, with respect to the polysaccharide or lignocellulose present. Water is gradually added to the reaction mixture after initiation of the hydrolysis reaction to achieve at least a total water content of 20 weight %. The water is added at a rate such that cellulose (or other polysaccharide) is not precipitated and hydrolysis is not substantially inhibited. In a specific embodiment, the total water content is gradually increased to between 20 weight % to 35 weight %. In other specific embodiments, the total water content is gradually increased to between 30 weight % to 45 weight %.

In the case of cellulose or other polysaccharide, hydrolysis is continued to achieve a maximum yield of glucose, while minimizing the production of undesired monosaccharide dehydration by-products, such as hydroxymethylfuran (HMF). In specific embodiments, the glucose yield from cellulose hydrolysis is equal to or greater than 50%. In specific embodiments, the glucose yield from cellulose hydrolysis is equal to or greater than 75%. In specific embodiments, the glucose yield from cellulose hydrolysis is equal to or greater than 85%. In specific embodiments, the hydrolysis reaction is carried out for 1-10 hours, more preferably 1-5 hours, and more specifically 2-3 hours. In a specific embodiment, the reaction is carried out at a temperature ranging from 100-110° C. for 1-4 hours and more specifically for 2-3 hours. The addition of water as described decreases the formation of undesired by-products of cellulose hydrolysis, specifically hydroxymethylfuran (HMF), which are believed at least in part to result from monosaccharide dehydration. In specific embodiments, the yield of HMF in the hydrolysis is 10% or less. In specific embodiments, the yield of HMF in the hydrolysis is 5% or less. The monosaccharide products of hydrolysis can be separated from ionic liquid and employed as a source of monosaccharide for any desired application. In a specific embodiment, the products of hydrolysis can be separated from ionic liquid and employed as a source of monosaccharide for growth of microorganisms and the production of fermentation products, such as ethanol. In an embodiment, the ionic liquid can be separated from the hydrolysis product, particularly by passage through an appropriate ion exchange column and the ionic liquid can optionally be recycled for reuse.

In the case of lignocellulose, the hydrolysis can be performed in one or more hydrolysis stages, with gradual water addition as described above, particularly in one hydrolysis stage or two hydrolysis stages. In a first hydrolysis stage, hydrolysis is continued to achieve a maximum yield of glucose, again while minimizing undesired by-products such as HMF. Other monosaccharides, such as xylose, may also be produced in the first stage by hydrolysis of polysaccharides other than cellulose, such as xylan, which may be present in the lignocellulose. Yield of monosaccharides other than glucose, e.g., xylose yield, in the first stage can be higher than 50%. In specific embodiments, glucose yield in the first stage typically can range from 10-30%. The hydrolysis product of the first stage can be diluted in excess water to precipitate remaining solids. The hydrolysis product of the first stage can be separated from the ionic liquid and employed as a source of monosaccharides in any desired application.

The precipitated solids, e.g., the remaining lignocellulose, from the first stage, can be subjected to a second stage of hydrolysis, as described above also with gradual water addition. The second stage is carried out to achieve a maximum yield of glucose, while minimizing undesired by-products. Combined glucose yields from the first and second stage hydrolyses are greater than 35%. In specific embodiments, combined glucose yields from the first and second stage hydrolyses are greater than 40%. In other embodiments, combined glucose yields from the first and second stage hydrolyses are greater than 50%. In specific embodiments, combined glucose yields from the first and second stage hydrolyses are greater than 60%. In specific embodiments, combined glucose yields from the first and second stage hydrolyses are 70% or more. Additional monosaccharides, such as xylose, may also be produced in the second stage. In specific embodiments, the first stage hydrolysis reaction is carried out for 1-4 hours, more specifically 1-3 hours. In specific embodiments, the second stage hydrolysis reaction is carried out for 1-5 hours, more specifically 3-4 hours. The first and second stages may be carried out at the same or different temperatures within the range 70 to 140° C. and more specifically 85 to 115° C. In specific embodiments, the first and second stage reactions are carried out at the same temperature. In a specific embodiment, the first and second stage reactions are carried out at about the same temperature in the range 100 to 110° C. In a specific embodiment, the first stage reaction is carried out at a temperature ranging from 100-110° C. for 1-4 hours and more specifically for 1-3 hours. In a specific embodiment, the second stage reaction is carried out at a temperature ranging from 100-110° C. for 1-5 hours and more specifically for 3-4 hours.

In specific embodiments, substantially complete hydrolysis of cellulose or other biomass polysaccharide is desired rather than partial hydrolysis to produce cellulose of lower DP than the starting cellulose. However, when the reaction is conducted to produce a monosaccharide-containing hydrolysis product, the reaction is preferably continued to achieve the highest yield or combined yield of the desired monosaccharide or mixture of monosaccharides.

The process of the invention does not require enzymes, such as cellulases, to achieve high monosaccharide yields, particularly high glucose yields. The process does not require the use of concentrated acid to achieve high monosaccharide yields, particularly high glucose yields. Lignocellulosic materials do not require chemical or enzymatic pretreatment to release cellulose or other biomass polysaccharides from lignin. Lignocellulosic materials are preferably subjected to mechanical pre-processing, chopping, grinding and/or milling prior to hydrolysis. In specific embodiments, lignocellulosic materials are milled to pass through a 100 mesh sieve. In specific embodiments, lignocellulosic materials are milled to pass through a 40 mesh sieve. The process of the invention can, however, be applied to any cellulose-containing materials, particularly lignocellulose, in which cellulose is at least partially separated from lignin by application of chemical or enzymatic pretreatment. Such cellulose-containing material can contain biomass polysaccharides other than cellulose, e.g., xylan. Lignocellulosic biomass can optionally be subjected to pre-treatment, including without limitation, contact with steam, liquid hot water, dilute acid, ammonia fiber expansion (AFEX), lime, and/or aqueous ammonia.

In specific embodiments herein the hydrolysis is conducted in certain ionic liquids as described herein in the absence of metal salts or metal catalyst.

In a specific embodiment, lignocellulosic materials are subject to a dilute acid treatment prior to hydrolysis by the method of this invention in ionic liquid with acid catalyst. The lignocellulosic materials can be contacted with dilute acid at appropriate temperature, pressure and time to typically achieve release of sugars from hemicelluloses in the lignocellulosic material. A slurry of lignocellulosic material in water can be formed to which an appropriately amount of dilute acid is added. The dilute acid pretreatment step is typically conducted at temperatures of 140-225° C., or more specifically at temperatures ranging from 185° C. to 210° C., for relative short times up to 10 min, preferably between 1-5 min. The dilute acid pretreatment can be conducted at ambient pressure, but preferably is conducted at pressures above ambient, ranging from ambient (approx. 1 atm) to 20 atm, preferably from 5 to 15 atm. In a specific embodiment, for dilute acid pretreatment, a biomass slurry in water is prepared which contains 20 to 40% by weight biomass. Acid is added to the slurry in an amount from 0.5 to 3% by weight and more specifically in amounts from 0.75% to 1.25%. Useful acids include mineral acids, particularly sulfuric acid, nitric acid, hydrochloric acid or phosphoric acid. After pretreatment, solids are separated from the aqueous liquid which contains some liberated sugars and the solids are subjected to hydrolysis in ionic liquid as described herein. The pretreated solids may be subject to drying to remove residual water prior to additional hydrolysis. As described herein below, any water remaining in the solid to be treated is considered when determining the amount of water to add to the reaction in ionic liquid. In a specific preferred embodiment, the process is conducted in two steps, the dilute acid step and a first hydrolysis stage as described herein to achieve desired high monosaccharide yields. The pretreatment step can be conducted in a batch reactor, a continuous reactor or in a flow-through reactor in which dilute acid flows through the solid biomass. As noted above, the first stage hydrolysis in ionic liquid is typically conducted at ambient pressure and temperatures ranging from about 70 to 140° C. and preferably 85 to 115° C. In a specific embodiment, the reaction is carried out at 100-110° C. Water is gradually added to the reaction after initiation of hydrolysis as noted above.

In the processes herein, water is added after acid catalyzed hydrolysis of cellulose is initiated to enhance glucose yields and minimize by-product generation, e.g., generation of HMF. The timing and amount of water addition is controlled to avoid cellulose precipitation, increase glucose yield (or yield of glucose combined with other monosaccharide) and minimize undesired dehydration by-product, e.g., HMF, formation. It will be readily appreciated that the initial reaction mixture may contain incidental low levels of total water that are in the ionic liquid, in the cellulose or lignocellulose, or otherwise enter the reaction vessel. Cellulose or lignocellulose itself can contain water dependent upon the source and physical form of the cellulose. Cellulose can, for example, contain 10-15% by weight water. Lignocellulosic materials subjected to pretreatment, for example dilute acid pretreatment, may contain water. Typically, such incidental water is present at levels of at most about 5 weight % of all reaction components. When incidental water levels are lower than about 5 weight % of all reaction components, water may optionally be added to the initial reaction mixture up to a level of about 5 weight % with respect to all reaction components. A portion of this initially added water may be added to facilitate acid addition. Any known amounts of water in the cellulose or added to the initial reaction mixture is considered in the determination of total water content, when water is added after the reaction is initiated. Initial water content is preferably sufficiently low to avoid any substantial cellulose precipitation. Cellulose precipitation can, for example, be detected visually by cloudiness in the ionic liquid. If the water content of the material to be hydrolyzed is over about 5% by weight, lignocellulosic materials or cellulose are optionally subjected to at least partial drying before hydrolysis to reduce water levels to about 5 weight % or less. Water-levels in material to be hydrolyzed can be determined by any method known in the art. Water levels in the material to be hydrolyzed should be sufficiently low to avoid precipitation, when the materials are added to and at least partially dissolved in ionic liquid.

Water addition to the reaction mixture after hydrolysis of cellulose is initiated can be controlled or regulated in various ways. Water may be added in a step-wise fashion of selected aliquots at selected times after reaction initiation. For example, 15 weight % water may be added at 10 min after reaction initiation to a reaction which initially contained 5 weight % water to achieve a target level of 20 weight % by 10 min after initiation. Alternatively, smaller aliquots of water may be added at regular intervals over the 10 min to achieve a target level of 20 weight % by 10 min after reaction initiation. In a specific embodiment, water additions may be made continuously at a selected rate over a selected interval to obtain the desired target level of total water content at a target time. Water additions are measured in terms of total weight % of water in the reaction mixture (including water that may be present in all reaction components, including material to be hydrolyzed.)

In embodiments, water is added to the reaction mixture to achieve a total water content of 5-20 weight % within 3-10 min after reaction initiation. In embodiments, water is added to the reaction mixture to achieve a total water content of 5-20 weight % within 3-10 min after reaction initiation and additional water is added to achieve a total water content of 20-35 weight % with 10-30 min after reaction initiation. In embodiments, water is added to the reaction mixture to achieve a total water content of 5-20 weight % within 3-10 min after reaction initiation, additional water is added to achieve a total water content of 20-35 weight % within 10-30 min after reaction initiation and additional water is added to achieve a water content of 35-45 weight % within 30-60 min after reaction initiation.

In specific embodiments, water is added to the reaction to achieve a total water content of 20 weight % with respect to the reaction mixture by 10 min after reaction initiation. In specific embodiments, water is added to the reaction to achieve a total water content of 20 weight % by 10 min after reaction initiation and additional water is added to achieve a total water content of 40-45 weight % by 60 min after reaction initiation. In specific embodiments, water is added to the reaction to achieve a total water content of 20 weight % by 10 min after reaction initiation and additional water is added to achieve a total water content of 30-35 weight % by 30 min after reaction initiation. In specific embodiments, water is added to the reaction to achieve a total water content of 20 weight % by 10 min after reaction initiation and additional water is added to achieve a total water content of 25 weight % by 20 min after reaction initiation. In specific embodiments, water is added to the reaction to achieve a total water content of 20 weight % by 10 min after reaction initiation, additional water is added to achieve a total water content of 30-35 weight % by 30 min after reaction initiation and yet additional water is added to achieve a total water content of 40-45 weight % by 60 minutes after reaction initiation.

In an embodiment, the catalytic acid is an organic or inorganic (mineral) acid, particularly an acid having a $pK_a$ of 1 or less in water at 25° C. In a specific embodiment, the catalytic acid is HCl. In a specific embodiment, the catalytic acid is $H_2SO_4$. In other embodiments the catalytic acid is HBr. In other embodiments, the acid is nitric acid. In yet other embodiments, the catalytic acid is trifluoroacetic acid. The catalytic acid may be a mixture of such acids. The acid may be employed in the form of an aqueous solution.

In an embodiment, the reaction mixture consists essentially of ionic liquid, catalytic acid, water (initial+added after initiation of hydrolysis) and the cellulose or lignocellulose. In an embodiment, the reaction mixture comprises ionic liquid, catalytic acid, water (initial+added after initiation of hydrolysis), the cellulose or lignocellulose and 25 weight % or less of a co-solvent. In an embodiment, the reaction mixture comprises ionic liquid, catalytic acid, water (initial+added after initiation of hydrolysis), the cellulose or lignocellulose and 10 weight % or less of a co-solvent.

The ionic liquid chloride salt dissolves cellulose and is believed to facilitate enhanced yield of glucose. Cellulose is introduced into the ionic liquid and vigorously stirred or mixed to aid dissolution. Optionally, the cellulose is stirred in the ionic liquid for at least an hour prior to adding acid and initiating the reaction. Enhanced glucose yield can be obtained if the cellulose is mixed with the ionic liquid for up to 3, up to 6 or up to 9 hours prior to initiation of reaction. This premixing of the ionic liquid with lignocellulose can be performed at ambient temperature or at a temperature above ambient up to 140 C, dependent upon the melting or softening point of the ionic liquid. The ionic liquid should be liquid or at least softened (so that it can be mixed). More specifically, the premixing can be performed at reaction temperature, specifically at a temperature between 70 and 140° C.

The ionic liquid chloride salt decrystallizes lignocellulose and at least partially dissolves cellulose therein. The ionic liquid is believed to facilitate enhanced yield of glucose. Lignocellulose is introduced into the ionic liquid and vigorously stirred or mixed to aid decrystalization or dissolution. Optionally, the lignocellulose is stirred in the ionic liquid for at least an hour prior to adding acid and initiating the reaction. Enhanced glucose yield can be obtained if the lignocellulose is mixed with the ionic liquid for up to 3, up to 6 or up to 9 hours prior to initiation of reaction. This premixing of the ionic liquid with lignocellulose can be performed at ambient temperature or at a temperature above ambient up to 140° C., dependent upon the melting or softening point of the ionic liquid. The ionic liquid should be liquid or at least softened (so that it can be mixed). More specifically, the premixing can be performed at reaction temperature, specifically at a temperature between 70 and 140° C.

In an embodiment, the ionic liquid is an organic salt in which the anion is chloride, trifluoroacetate, trichloroacetate, tribromoacetate or thiocyanate and in which cellulose is at least partially soluble. The ionic liquid is a liquid at the reaction temperature and pressure. In a specific embodiment, the ionic liquid is a liquid at the reaction temperature at ambient pressure. In an embodiment, the ionic liquid chloride salt is an imidazolium salt. In an embodiment, the ionic liquid chloride salt is a C1-C6 alkyl imidazolium salt. In specific embodiments, the ionic liquid is a salt of an [EMIM]$^+$ or [BMIM]$^+$ or 1-ethyl-2,3-dimethylimidazolium cation. In another embodiment, the ionic liquid is a pyridinium salt. In another embodiment, the ionic liquid salt is a C1-C6 alkyl pyridinium salt. In specific embodiments, the ionic liquid is a 1-alkylpyridinium salt, particularly where the alkyl group is a C1-C6 alkyl group. In specific embodiments, the ionic liquid salt is 1-ethylpyridinium cation salt or 1-butyl-4-methylpyridinium cation salt. Additional organic cations of ionic liquids are described in US 2009/0062524, WO2009030950, WO2009030849, US20090020112, WO2008112291, US20080227162 and WO2009024607, each of which is incorporated by reference herein for descriptions of such cations.

In a specific embodiment, the ionic liquid is an organic chloride salt in which cellulose is at least partially soluble. The ionic liquid is a liquid at the reaction temperature at ambient pressure. In an embodiment, the ionic liquid chloride salt is an imidazolium chloride. In an embodiment, the ionic liquid chloride salt is a C1-C6 alkyl imidazolium chloride. In specific embodiments, the ionic liquid chloride salt is [EMIM]Cl or [BMIM]Cl or 1-ethyl-2,3-dimethylimidazolium chloride. In another embodiment, the ionic liquid chloride salt is a pyridinium chloride. In another embodiment, the ionic liquid salt is a C1-C6 alkyl pyridinium chloride. In specific embodiments, the ionic liquid salt is a 1-alkylpyridinium salt, particularly where the alkyl group is a C1-C6 alkyl group. In specific embodiments, the ionic liquid salt is 1-ethylpyridinium chloride or 1-butyl-4-methylpyridinium chloride. Additional organic cations of ionic liquids are described in US 2009/0062524, WO2009030950, WO2009030849, US20090020112, WO2008112291, US20080227162 and WO2009024607, each of which is incorporated by reference herein for descriptions of such cations.

In an embodiment, the ionic liquid is an organic salt wherein the anion is the conjugate base of an acid having a pKa less than 1, for example chloride is the conjugate base of HCl which has a pKa of −1 and trifluoroacetate is the conjugate base of tifluoroacetic acid which has a pKa of 0.3. More specifically in this embodiment, the cation of the ionic liquid is an imidazolium. In an embodiment, the cation is a C1-C6 alkyl imidazolium. In specific embodiments, the cation is [EMIM]+ or [BMIM]+ or 1-ethyl-2,3-dimethylimidazolium. In another embodiment, the cation is a pyridinium. In another embodiment, the cation is a C1-C6 alkyl pyridinium. In specific embodiments, the cation is a 1-alkylpyridinium salt, particularly where the alkyl group is a C1-C6 alkyl group. In specific embodiments, the cation is a 1-alkylpyridinium ion, particularly where the alkyl group is a C1-C6 alkyl group. In specific embodiments, the cation is 1-ethylpyridinium or 1-butyl-4-methylpyridinium. C1-C6 alkyl groups include straight chain, branched and cyclic alkyl groups. Specific alkyl groups are methyl, ethyl, n-propyl, and n-butyl groups.

In application to cellulose or other biomass polysaccharides, in an embodiment the concentration of biomass polysaccharide in the initial reaction mixture ranges from 1-25 weight % and more specifically from 5-10 weight %, from 5-25 weight %, from 10-25 weight %, from 15-25 weight %, or from 20-25 weight %.

In application to lignocellulose, in an embodiment the concentration of lignocellulose in the initial reaction mixture ranges from 1-25 weight % and more specifically from 5-10 weight %, from 5-25 weight %, from 10-25 weight %, from 15-25 weight %, or from 20-25 weight %.

The method of the invention is applicable to any lignocellulosic material, particular that which is derived from biomass, including without limitation, wood or woody material, paper waste, plants, crops and agricultural residue (e.g., corn stover, wheat straw, barley straw, soya stalk, sugar cane bagasse), leaves and stalks of non-woody plants, and grasses (switch grass, Miscanthus). In an embodiment, the method is applicable to lignocellulosic material containing 20-50% dry weight cellulose.

In an embodiment, the hydrolysis product(s) formed in the ionic liquid can be separated from the ionic liquid using a strong cation exchange resin. In an embodiment, the strong cation exchange resin is a cross-linked polystyrene cation exchange resin, where the resin is cross-linked with divinylbenzene and treated with sulfuric acid to produce a strong acid resin. The resin can be formed by polymerizing vinylbenzyl chloride with divinylbenzene and treating with sodium sulfite to produce a strong acid resin. Useful resins include without limitation, PCR833 (Purolite Inc.), Dowex 50WX4 and Dowex Monosphere 99 (Dow Chemical), Amberlite 1310CR (Rohm & Haas), and Diaion UBK555 (Mitsubishi Chemical). To recover the ionic liquid, the resin must be exchanged prior to its use in the separation with the cation of the ionic liquid, such as the 1-ethyl-3-methylimidazolium cation. In an embodiment, the hydrolysis product in the ionic liquid is adsorbed on the resin and eluted with water. In an embodiment the resin is heated to 40-70° C. In a specific embodiment the resin is heated to 65° C.

In a specific embodiment, the invention provides a method for hydrolysis of lignocellulose to produce monosaccharides (including mixtures of monosaccharides) which comprises at least two stages of hydrolysis carried out in an ionic liquid as described herein which at least in part solubilizes cellulose. In this specific embodiment, residual solid is removed from the first hydrolysis stage for passage to the second hydrolysis stage. Hydrolysis product(s) from the first stage is separated from the ionic liquid employing passage through a strong cation exchange resin, which resin has been exchanged with the cation of the ionic liquid used. Separated ionic liquid is returned for reuse in the second stage hydrolysis. When more than two stages of hydrolysis are conducted, hydrolysis product(s) from the preceding stage are separated from ionic liquid which is then returned for reuse in the next stage. The separated hydrolysis products from each stage are, optionally combined, and employed as a source of monosaccharides. In more specific embodiments, the ionic liquid is one in which the anion of the ionic liquid is chloride, trifluoroacetate, trichloroacetate, tribromoacetate or thiocyanate.

In a specific embodiment, the invention provides a method for hydrolysis of lignocellulose to produce monosaccharides (including mixtures of monosaccharides) which comprises one hydrolysis step carried out in an ionic liquid which at least in part solubilizes cellulose, as described herein. This method also includes at least one pre-treatment step of the lignocellulosic biomass prior to hydrolysis. The pretreatment can including without limitation, contact with one or more of steam, liquid hot water, dilute acid, ammonia fiber expansion (AFEX), lime, and/or aqueous ammonia. Pre-treatment can be conducted in one or more steps, however, to decrease processing costs, pretreatments steps are preferably minimized. In a specific embodiment, only one pretreatment step is applied to minimize cost. In a specific embodiment, the pretreatment step is treatment of biomass with dilute acid in water at about 140-225° C., more specifically between 185 to 210° C. and preferably 190 to 200° C., for up to 10 minutes, more preferably up to 5 minutes and more specifically from 1-10 minutes or preferably 1-5 minutes. Such pretreatment step or steps preferably hydrolyze the hemicellulose off of the biomass leaving cellulosic solids which are carried on to hydrolysis in ionic liquid as described herein to release glucose (or other monosaccharide). Any monosaccharide released by pretreatment is combined with monosaccharide generated by hydrolysis in ionic liquid. Monosaccharides are separated from ionic liquid and ionic liquid is recycled for hydrolysis of additional materials.

The invention additionally provides a process for hydrolysis of acid-pretreated biomass which comprises a step of hydrolysis in ionic liquid as described herein with addition of water as described herein after initiation of hydrolysis as described herein.

In a specific embodiment, the hydrolysis products of the methods of this invention are employed as a monosaccharide feedstock for growth or one or more microorganism, in particular for growth of one or more bacteria or yeast. In specific embodiments, the microorganisms are ethanologenic or solventogenic microorganisms which ferment such hydrolysis product to generate ethanol, propanol, butanol, acetone, various organic acids or mixtures thereof. The invention also provided fermentation feedstock containing low levels of undesired sugar dehydration by products, such as HMF. Levels of such dehydration products in fermentation feedstocks of this invention are less than 20% by weight and are preferably 10% by weight or less, 5% by weight or less or 3% by weight or less.

DETAILED DESCRIPTION OF THE INVENTION

This invention is at least in part based on the demonstration of an efficient system for polysaccharide hydrolysis as well as means to separate and ferment the resulting sugars. The method of this invention is generally applicable to biomass polysaccharides, i.e., polysaccharides found in biomass, such as cellulose, xylan, mannan, galactan, and arabinan. The method is also applicable to lignocellulosic biomass. The method is also applicable to pre-treated lignocellulosic biomass, particularly such biomass pre-treated with dilute acid.

Figure 1:
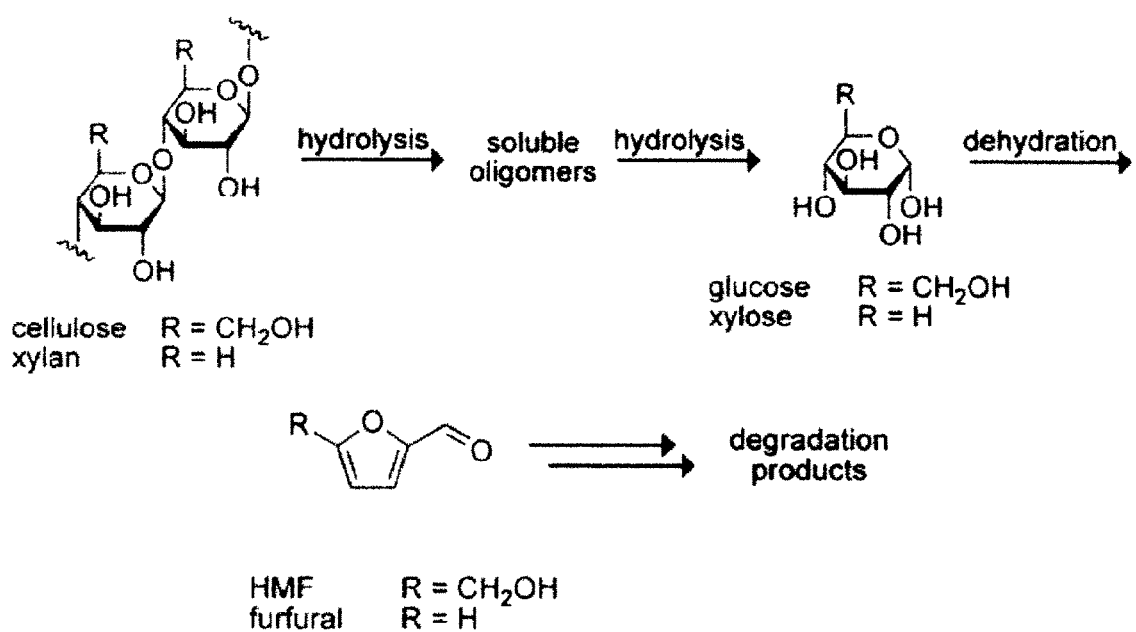
FIG. 1 is a chemical scheme showing hydrolysis reactions of cellulose and xylan. Chemical hydrolysis of cellulose and hemicellulose into monomeric sugars proceeds through oligomers and is accompanied by side reactions that form furans and other degradation products.
Figure 2:
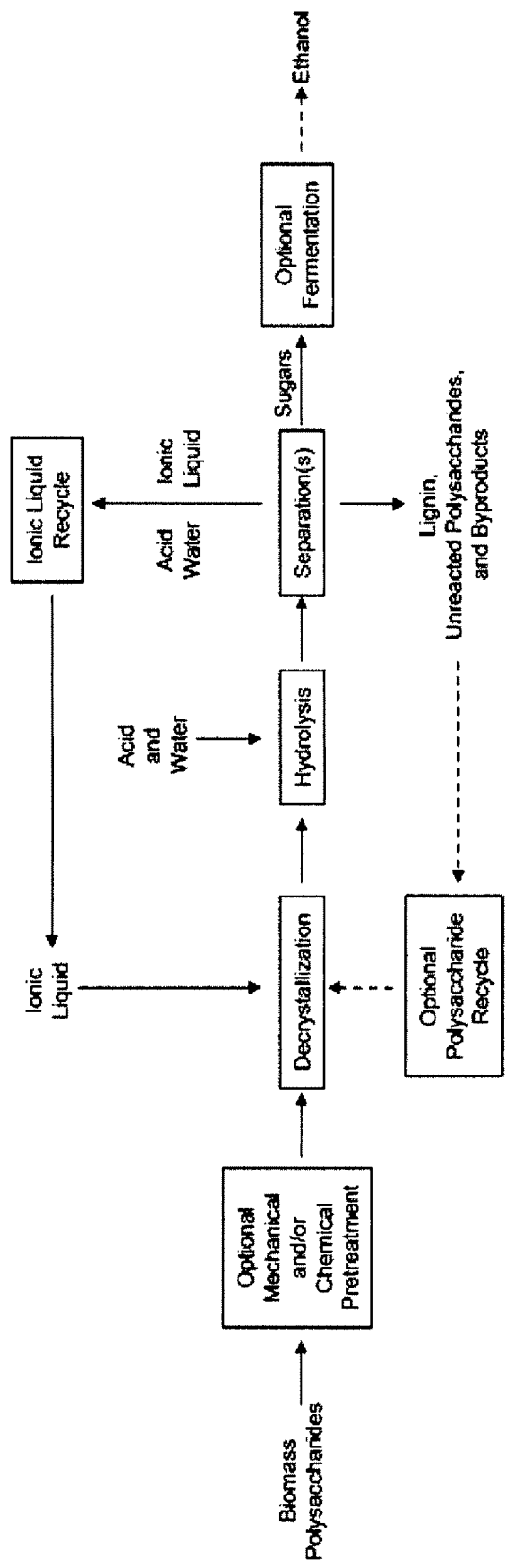
FIG. 2 is a schematic flow chart for an integrated process for biofuel production using ionic liquid biomass hydrolysis. In a specific embodiment, separation can be conducted employing ion exchange methods. The process includes optional mechanical and/or chemical pretreatment steps, optional, but preferred, decrystallization in ionic liquid, hydrolysis in ionic liquid with controlled water addition; and separation and optional, but preferred, recycle of ionic liquid. Product sugars are optionally directed to fermentation to product desirable products, such as ethanol.

By balancing polysaccharide, e.g., cellulose, solubility and reactivity with water, sugars are produced from lignocellulosic biomass in yields that are several times higher than those achieved previously in ionic liquids and approach those of enzymatic hydrolysis. Furthermore, the hydrolyzate products are readily converted into ethanol or other desirable products by microorganisms. The invention provides an improved method for biomass hydrolysis to generate fermentable sugars. The invention also provides an integrated process for chemical hydrolysis of biomass for biofuel production (FIG. 2). First, lignocellulosic biomass, such as corn stover, is optionally pretreated mechanically and/or chemically, for example, by dilute acid treatment, the biomass is then optionally, but preferably decrystallized through mixing with ionic liquid. The biomass is then subject to acid-catalyzed hydrolysis in ionic liquid with controlled addition of water as described herein. The residual lignin and cellulose solids are optionally subjected to a second hydrolysis stage, while the liquid hydrolyzate is separated from ionic liquid, for example, using ion-exclusion chromatography. Additional stages of hydrolysis in ionic liquid can be conducted if desired. Ionic liquid recovered in the ion exclusion step is optionally stripped of water and recycled, while hydrolyzate sugars are optionally fermented into fuels and/or other bioproducts.

Hydrolyzate sugars produced by the hydrolysis method herein can be employed in a variety of applications in addition to fermentation. Lignocellulosic biomass materials can optionally be subjected to pre-treatment steps which may further improve processing.

The invention thus provides a method of making a fuel, such as ethanol or butanol or other bioproducts which comprise the improved biomass hydrolysis step of this invention. Fermentation processes for making ethanol, butanol and other useful products from feedstock containing monosaccharides are known in the art. For example, Mosier et al. [56] provides a recent review of biomass conversion to ethanol and pretreatment and hydrolysis of lignocellulosic materials for such processes. This reference is incorporated by reference herein in its entirety for descriptions of such fermentation processes.

In comparison to extant enzymatic and chemical approaches to biomass hydrolysis, the ionic liquid system of this invention has many attractive features. Like concentrated acid processes, it uses inexpensive chemical catalysts rather than enzymes and avoids an independent pretreatment step. Working in concert, the ionic liquid system, e.g., [EMIM]Cl and HCl, produce high sugar yields in hours at just 105° C., whereas enzymatic hydrolysis can take days [12] and many pretreatment methods require temperatures of 160-200° C. [10]. Also, lignocellulose solubilization by the ionic liquid allows processing at high concentrations, which can be a problem in enzymatic hydrolysis. On the other hand, this ionic liquid process improves on typical acid hydrolysis methods by avoiding the use of hazardous concentrated acid. Using catalytic amounts of dilute acid removes the complexity and danger of recycling large volumes of concentrated acid. The ionic liquid used in its place is likely to be far easier to handle. Despite these differences, the ionic liquid process is similar to commercial processes using concentrated acid hydrolysis [16,23]. Consequently, it can exploit proven engineering and equipment for facile scale-up.

The term "ionic liquid" as used herein is intended to have its broadest art-recognized meaning that is not inconsistent with the disclosure herein. An ionic liquid is a salt that melts near or below ambient room temperature. For use in the methods herein the ionic liquid is liquid at the reaction temperature. The term "chloride-containing ionic liquid" refers to an ionic liquid in which the anion of the salt is chloride. Analogous terms "specific anion-containing ionic liquid" refers to an anionic liquid in which the anion of the salt is the anion specified. Similarly, a group of ionic liquids can be described by naming a class or group of cations of the ionic liquid, e.g., pyridinium-containing ionic liquid. The ionic liquid useful in this invention is one in which cellulose is at least in part soluble, i.e., is soluble to some measurable extent. Preferably the ionic liquid is one in which up to about 5-25 weight % or more of the cellulose contacted is soluble. More preferably the ionic liquid is one in which up to about 25 weight % or more of the cellulose is soluble. Lignocelluosic materials need not be soluble in the ionic liquid. Such materials may be decrystallized, swollen, partially solubilized or structurally disrupted by contact with and mixing with the ionic liquid. A number of ionic liquids have been shown in the art to dissolve cellulose. A number of ionic liquids are commercially available or can be prepared by art-known methods. The methods herein specify the addition of acid catalyst to the ionic liquid to carry out the hydrolysis reaction. Ionic liquids as purchased or prepared may, however, contain some amount of acid. In preferred embodiments, for consistency of reaction, ionic liquids that do not contain acid residue or contamination are preferred. When the ionic liquid as purchased or prepared contains acid, no acid or reduced levels of acid are required to carry out the hydrolysis reaction.

Although not required by the methods of this invention, a suitable co-solvent can be employed in combination with the ionic liquid. Co-solvents can, for example, be added to the ionic liquid to reduce the viscosity of the reaction mixture or to enhance mixing of reaction components or enhance flow of the reaction mixture. Suitable co-solvents include polar aprotic solvents, including among others dialkylacetamides, in particular dimethylacetamide (DMA), diethylacetamide (DEA) or acetonitrile. In other embodiments, the co-solvent is a dialkylformamide, including dimethylformamide; a pyrrolidone, including an alkyl- or N-alkyl-substituted pyrrolidinone or more specifically including methylpyrrolidone, or 1-ethyl-2-pyrrolidinone; sulfolane; a dialkyl sulfoxide, particularly dimethylsulfoxide; dioxane; an alkyl or N-alkyl substituted lactam, including N-methylcaprolactam; a dialkyl propionamide, including N,N-dimethylpropionamide; an alcohol having 6-12 carbon atoms, including n-butanol; 1-pyrrollidine carboxaldehyde; or miscible mixtures thereof. Preferred co-solvents include DMA, N-methylpyrrolidone and acetonitrile. Pyridine is not a preferred co-solvent of this invention. Preferred co-solvents are anhydrous. In specific embodiments, the co-solvent is present at levels less than 25 weight % of the reaction mixture. In other embodiments, the co-solvent is present at levels less than 10 weight % of the reaction mixture. In other embodiments, the co-solvent is present at levels less than 5 weight % of the reaction mixture. In specific embodiments, the co-solvent represents 1-25 weight % of the reaction mixture. In specific embodiments, the co-solvent represents 1-10 weight % of the reaction mixture. In specific embodiments, the co-solvent represents 1-5 weight % of the reaction mixture.

In specific embodiments, the cation of the ionic liquid is an organic cation, particularly containing at least one positively charged nitrogen atom. In specific embodiments, the ionic liquid is an alkylimidazolium ionic liquid, more particularly an alkylimidazolium chloride ionic liquid. In additional specific embodiments, the ionic liquid is a 1,3-dialkyl-imidazolium chloride or a 1,2,3-trialkylimidazolium chloride. In specific embodiments, the alkyl substituents have 1-6 carbon atoms and more specifically 1-3 carbon atoms. In more specific embodiments, the ionic liquid is [EMIM]Cl (1-ethyl-3-methylimidazolium chloride), [BMIM]Cl (1-butyl-3-methylimidazolium chloride), or 1-ethyl-2,3-dimethylimidazolium chloride, or a mixture thereof. In specific embodiments, the ionic liquid is an alkylpyridinium ionic liquid, more particularly an alkylpyridinium chloride ionic liquid. In additional specific embodiments, the ionic liquid is a 1-alkylpyridinium ionic liquid or a 1,4-dialkylpyridinium chloride. In more specific embodiments, the ionic liquid is 1-ethylpyridinium chloride, 1-butyl-4-methylpyridinium chloride, or a mixture thereof. Additional ionic liquids useful in the invention particularly those in which chloride is the anion of the salt of the ionic liquid, are provided in US 2008/0033187. Additional organic cations of ionic liquids are described in US 2009/0062524, WO2009030950, WO2009030849, US20090020112, WO2008112291, US20080227162 and WO2009024607, each of which is incorporated by reference herein for descriptions of such cations.

Additional, organic cations of ionic liquids useful in the invention include 1,3-dimethylimidazolium, 1-hexyl-3-methylimidazolium and generally 1,3-dialklyimidazolium cations with alkyl chains with 6 or fewer carbons; 1-R'-3-alkyllimidazolium, where R is a an alkenyl group having 1-6 carbon atoms, such as an allyl group, or an alkyl group substituted with an aryl group, particularly a phenyl group, which is optionally substituted, such as 1-benzyl-3-alkyllimidazolium or optionally substituted 1-benzyl-3-alkylimidazolium; 1,3-dialkylpyrrolidinium, where the alkyl groups may be same or different and have 1-6 or 1-3 carbon atoms, such as 1-butyl-3-methylpyrrolidinium; and N-substituted pyridinium cations such as those substituted with alkyl groups having 1-6 or 1-3 carbon atoms, such as 3-methyl-N-butylpyridinium.

The following cations are not preferred for use in the methods herein due to expected poor cellulose solubility: 1-octyl-3-methylimidazolium (and higher alkyl chains); 1-octyl-3-methylpyrrolidinium (and higher alkyl chains) N-octylpyridinium (and higher alkyl chains).

The term "biomass polysaccharide substrate" is used generically herein to refer to a biomass polysaccharide, to lignocellulose or lignocellulosic biomass containing a biomass polysaccharide. A "biomass polysaccharide" refers to any polysaccharide that derives from biomass and specifically include among others, cellulose, mannan, xylan, galactan, and arabinan. A given lignocellulose or lignocellulosic biomass may contain more than one biomass polysaccharide. Hydrolysis of a given biomass polysaccharide may result in a mixture of monosaccharides.

The term "lignocellulose" or "lignocellulosic material or biomass" is used herein to refer to materials from any source containing lignin and cellulose. Lignocellulose and lignocellulosic material may contain other biomass polysaccharides, such as hemicellulose, xylan, arabinan, or mannan. Typically, cellulose and other biomass polymers in such materials are tightly bound to lignin. Lignocellulose or lignocellulosic material may be pre-treated by physical methods (grinding, chopping or mashing) or by chemical or biological (e.g., enzymatic) methods as are known in the art which may increase the accessibility of cellulose or other biomass polysaccharide to hydrolysis. Such chemical or biological pre-treatments are however, not required for the practice of this invention. Lignocellulosic materials include, among others, wood residues, paper waste, agricultural residue and energy crops (e.g., woody grasses, such as switch grass or Miscanthus). Lignocellulose and lignocellulosic material may contain water. Preferred biomass polysaccharide substrates for this invention contain less than 20% by weight of water and more preferably contain 15% by weight or less of water. The water-content of such materials can be lowered by methods that are known in the art.

The term "cellulose" is used broadly herein to include cellulose from any source and includes alpha-cellulose, beta-cellulose and gamma-cellulose and mixtures thereof. Cellulose can be characterized by its degree of polymerization (DP, average number of anhydroglucose units) which can range from tens of thousands to hundreds, e.g., 10,000-12,000 to 300. Cellulose as used herein also refers to underivatized cellulose or derivatives of cellulose, such as ethyl- or methylcellulose, hydroxyalkyl cellulose (e.g., hydroxypropyl cellulose), carboxymethylcellulose, or mixtures thereof. In specific embodiments, the method of this invention is particularly useful for cellulose or cellulose derivatives which are water-insoluble. In specific embodiments, the method of this invention is particularly useful for cellulose derived without chemical modification from natural sources. Cellulose preferred for this invention contains less than 20% by weight of water and more preferably contains 15% by weight or less of water. The water-content of cellulose can be lowered by methods that are known in the art.

The term "hydrolysis product" is used herein to refer to the at least predominantly monosaccharide containing product generated in the methods of this invention. The hydrolysis product will typically be generated as an aqueous solution of one or more monosaccharides. The hydrolysis product may also contain disaccharides (such as cellobiose) and relatively low levels of sugar oligomers (e.g., tri-hexa-saccharides) preferably less than 10% by weight). Preferably, the hydrolysis product contains only minor amounts of the products of monosaccharide dehydration, e.g., furans, such as furfural or HMF, such that the hydrolysis product is not toxic to microorganisms and as such is useful as a monosaccharide feedstock. Preferably, the hydrolysis product contains only low levels of potentially toxic hydrolysis by-products, such as levulinic acid, that the hydrolysis product is not toxic to microorganisms and as such is useful as a monosaccharide feedstock. In specific embodiments, the hydrolysis product (with water removed) contains 75% by weight or more of one or more monosaccharides. In specific embodiments, the hydrolysis product (with water removed) contains 90% by weight or more of one or more monosaccharides. In specific embodiments, the hydrolysis product (with water removed) contains 95% by weight or more of one or more monosaccharides. In specific embodiments, the hydrolysis product contains less than 10% by weight of furfural, HMF, or levulinic acid. In specific embodiments, the hydrolysis product contains less than 5% by weight of furfural, HMF, or levulinic acid. In specific embodiments, the hydrolysis product contains less than 2.5% by weight of furfural, HMF, or levulinic acid. In specific embodiments, the hydrolysis product contains less than 10% by weight of combined furfural, HMF, and levulinic acid. In specific embodiments, the hydrolysis product contains less than 5% by weight of combined furfural, HMF, and levulinic acid. In specific embodiments, the hydrolysis product contains less than 2.5% by weight of combined furfural, HMF, and levulinic acid.

In the methods herein water is added to the hydrolysis reaction mixture after "initiation" of the hydrolysis reaction to improve monosaccharide yields and decrease undesired by-product formation. Reaction is typically initiated when a sufficient amount of acid catalyst is combined with polysaccharide or lignocellulose and ionic liquid and the mixture is heated to a temperature typically above ambient sufficient for hydrolysis to occur. Typically a temperature of about 70 C or more is required for hydrolysis to occur. Typically about 5 weight % of acid catalyst relative to polysaccharide or lignocellulosic material is required for hydrolysis to occur. Initiation of hydrolysis can be triggered in various ways. For example, it can be triggered by addition of acid to a mixture of polysaccharide or lignocellulose in ionic liquid held at the reaction temperature. Alternatively, it can be triggered by raising the temperature of a mixture of polysaccharide or lignocellulose in ionic liquid and acid to the reaction temperature. Alternatively, it can be triggered by adding polysaccharide or lignocellulose to a mixture of ionic liquid and acid at the reaction temperature. Alternatively, triggering requires the interaction of acid with polysaccharide or lignocellulosic material at reaction temperature, so that initiation may be triggered by sufficient mixing of the reaction components. Alternatively, a combination of such triggering can be used. In a preferred embodiment, reaction is triggered by addition of acid or raising of the temperature of a mixture of polysaccharide or lignocellulose in ionic liquid. The amount of water that is added in any addition during the reaction is not intended to inhibit or quench hydrolysis. However, when it is desired to stop or quench the hydrolysis reaction, e.g., when a desired yield of glucose is achieved, one way in which the reaction may be quenched is by addition of a large excess of water.

In specific embodiments, the acidity of the batch of ionic liquid employed may be sufficient for cellulose hydrolysis without the requirement for adding acid catalyst. It is believed that the acidity of ionic liquids can vary from batch to batch and as a function of the source (e.g., the manufacturer of a given commercial ionic liquid or the method of synthesis employed to prepare the ionic liquid compound). The amount of acid may vary dependent upon the methods employed to make or to purify the ionic liquid. Thus, ionic liquids that are sufficiently contaminated with acid may not require addition of acid catalyst or may require addition of lower levels of acid catalyst than are described herein. One of ordinary skill in the art will recognize that there are well-known methods for assessing acidity which can be applied to assessing the acidity of ionic liquids prior to their use in the methods of this invention. One method that is applicable is a standard acid-base titration.

It will be appreciated by one of ordinary skill in the art that the amount of acid catalyst and the temperature at which reaction is initiated will depend upon the substrate being hydrolyzed, the type of acid and other specifics of the reaction conditions, including, as noted above, the source of the ionic liquid employed. The amount of water added is controlled to avoid precipitation of polysaccharide and minimized by-product formation, particularly from dehydration of saccharides. The order of addition of catalyst and raising temperature is not particularly constrained, however, typically the mixture in ionic liquid is heated to reaction temperature and the acid is then added. It will be appreciated that the reaction components are typically mixed to initiate reaction and that reaction may be inhibited, particularly when the reaction mixture is viscous, if the reaction mixture is not sufficiently mixed or agitated. Typically, the mixture in ionic liquid is vigorously mixed and heated to reaction temperature prior to acid addition and vigorous mixing is continued on addition of acid catalyst. Mixing of the reaction mixture is typically continuous as additional water is added.

The hydrolysis reaction or reaction stages are carried out at temperatures above ambient. The reaction is typically carried out at ambient pressure and at temperatures ranging from about 70 to 140° C., preferably 85 to 115° C. and more specifically at 100-110° C. The reaction may be heated by any known method, including thermal heating, microwave heating, infrared heating or ultrasound heating. It may be found beneficial to carry out the reaction under increased pressure or sub-ambient pressure and if non-ambient pressures are used one of ordinary skill in the art recognizes that the reaction temperatures can be adapted for such chosen pressure. The reaction can be carried out in air (ambient atmosphere). It may be found beneficial to carry out the reaction in a more inert atmosphere, such as under nitrogen or under inert gas. Exclusion of oxygen is not, however, a requirement of the methods of this invention.

Although not required by the method, biomass polysaccharide substrate, e.g., lignocellulosic materials (biomass), can be subjected to various pretreatment steps prior to hydrolysis in ionic liquid as described herein. Mechanical pretreatment involving chopping and/or grinding to a desired particle size can be applied as is known in the art. Additional pretreatment processes, include among others, exposure to steam, hot water, dilute acid, AFEX, ARP and exposure to lime. The goal of such pretreatment is to release cellulose and hemicellulose from lignin. Mosier et al. [56] provides a recent review of such pretreatment steps and is incorporated by reference herein in its entirety for this description.

The chemical hydrolysis method of this invention offers flexibility for an integrated biomass conversion process. Because the ionic liquid solvent makes biomass polysaccharides readily accessible for chemical reactions, this process is likely to be compatible with a broad range of biomass feedstocks. Downstream, the sugars produced by ionic liquid hydrolysis are flexible feedstocks for production of a nearly infinite range of fuels and chemicals. *E. coli*, which readily use the hydrolyzate sugars, have been engineered to produce not only fuel ethanol but also 1-butanol, 2-butanol, branched alcohols, fatty acids, isoprenoids, and even hydrogen [47-49]. Furthermore, the aqueous stream of sugars can also be converted by catalytic processes into fuels or chemical intermediates [50-51]. In contrast with enzymatic hydrolysis reactions that often require coupling to fermentation (simultaneous saccharification and fermentation) to prevent product inhibition, this chemical process can be paired with any downstream conversion. Finally, the lignin recovered from ionic liquid biomass hydrolysis can be a valuable coproduct. Jones and coworkers noted that the lignin residue from biomass hydrolysis in ionic liquids is relatively unmodified, suggesting that it could be an excellent feedstock for high-value lignin products [31, 52]. As a result, our process, which uses simple chemical reagents to overcome biomass recalcitrance and liberate valuable sugars, has the potential to underpin a versatile biorefinery.

In view of the foregoing the invention provides methods for production of various fuels and chemicals which comprise a step of hydrolysis of a biomass polysaccharide substrate to produce a feedstock containing monosaccharides, particularly glucose, for subsequent production of fuels or chemicals. The hydrolysis, as described herein, in turn comprises the steps of: contacting the biomass polysaccharide substrate with an ionic liquid, as described herein, wherein the anion of the ionic liquid is chloride, trifluoroacetate, trichloroacetate, tribromoacetate or thiocyanate to at least in part solubilize the polysaccharide in the ionic liquid; heating the mixture to reaction temperature and adding an acid catalyst in an amount sufficient to initiate hydrolysis of the polysaccharide; and adding water to the reaction mixture after initiation of the hydrolysis reaction such that the total water content is at least 20 weight %. The hydrolysis comprises addition of water as described herein to avoid precipitation of polysaccharide and inhibition of hydrolysis and to minimize dehydration of sugar (e.g., monosaccharide) products. In specific embodiments, the invention provides methods for production of ethanol, 1-butanol, 2-butanol, branched alcohols, fatty acids, fatty acid esters, isoprenoids, and even hydrogen [47-49] which employ hydrolyzate sugars.

The invention provides improved fermentation feedstocks from biomass by the hydrolysis process described herein. The feedstocks produced generally contain low levels of undesired sugar dehydration products such as HMF which are generally undesirable in such feedstocks used for fermentation, particularly bacterial fermentation. Improved feedstocks of this invention contain 20% or less by weight of such dehydration products, particularly HMF. Improved feedstocks herein contain 15% by weight or less, 10% by weight or less, 5% by weight or less, 2% by weight or less or 1% by weight or less of such dehydration products, such as HMF.

The invention provides improved fermentation and bioconversion processes in which the feedstock for the fermentation or bioconversion is made by the hydrolysis process of this invention. Furthermore, the aqueous stream of sugars produced by hydrolysis of this invention can also be converted by catalytic processes into fuels or chemical intermediates [50, 51]. Thus, the invention provides improved catalytic processes for making fuels or chemicals employing a feedstock produced by the hydrolysis reaction of this invention. In contrast with enzymatic hydrolysis reactions that often require coupling to fermentation (simultaneous saccharification and fermentation) to prevent product inhibition, the chemical hydrolysis process of this invention can be paired with any downstream conversion. Additionally, lignin recovered from ionic liquid biomass hydrolysis of this invention can be a valuable co-product. As noted by Jones and coworkers, the lignin residue from biomass hydrolysis in ionic liquids is relatively unmodified, indicating that it could be an excellent feedstock for high-value lignin products [31, 52]. As a result, the invention also provides methods of converting lignin to such lignin products employing the hydrolysis process of this invention to generate a lignin feedstock for such processes.

When a group of chemical species is disclosed herein, it is understood that all individual members of that group and all subgroups, including any structural isomers, enantiomers, and diastereomers of the group members, are disclosed separately. When a Markush group or other grouping is used herein, all individual members of the group and all combinations and subcombinations possible of the group are intended to be individually included in the disclosure.

Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, pressure range, a time range, a range of values for a given variable, or a composition or concentration range, all intermediate ranges and subranges, as well as all individual values included in the ranges given are intended to be included in the disclosure. Unless otherwise noted all ranges noted herein are inclusive of the lower and upper range value listed. It will be understood that any subranges or individual values in a range or subrange, that are included in the description herein, can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrequited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of. Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

One of ordinary skill in the art will appreciate that starting materials, reagents, synthetic methods, purification methods, analytical methods, assay methods, substrates, and solids other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference herein in their entirety. In case of any discrepancy between disclosure in a reference cited and that of this specification, the specification takes precedence. Some references provided herein are incorporated by reference to provide details concerning sources of starting material, methods of synthesis, methods of purification, methods of analysis; as well as additional uses of the invention.

THE EXAMPLES

Seeking a more effective hydrolysis process, the fundamental reactivity of cellulose and sugars under acidic conditions in ionic liquids was investigated. we began by reacting cellulose under similar conditions to Li and Zhao [28] with $H_2SO_4$ and HCl in [EMIM]Cl. Interestingly, the production of 5-hydroxymethylfurfural (HMF) as well as moderate yields of glucose were observed (Table 1). Cellulose was reacted in [EMIM]Cl at 105° C. after its dissolution at 105° C. for 12 h. In Table 1, HCl loading is relative to cellulose weight; yields are molar yields based on HPLC analysis, and are relative to the glucose monomers contained in the cellulose; nod means not determined. In row one (labeled a) the acid used was $H_2SO_4$.

The aldehyde functionality of HMF, a sugar dehydration product, interferes with the DNS assay as was used by Zhao and coworkers [35], and likely caused their TRS yields to be far higher than their actual sugar yields. The production of HMF at the expense of glucose suggested that either cellulose was being transformed directly into HMF or glucose from hydrolysis was being dehydrated to form HMF.

TABLE 1

Hydrolysis of cellulose in [EMIM]Cl.

| cellulose (wt %) | HCl (wt %) | water content (wt %) time (min) | | | | | | time (h) | glucose yield (%) | HMF yield (%) |
|---|---|---|---|---|---|---|---|---|---|---|
| | | 0 | 5 | 10 | 20 | 30 | 60 | | | |
| 5 | 20[a] | 5 | 5 | 5 | 5 | 5 | 5 | 1 | 40 | 19 |
| 5 | 20 | 5 | 5 | 5 | 5 | 5 | 5 | 1 | 45 | 17 |
| 5 | 20 | 5 | 33 | 33 | 33 | 33 | 33 | 1 | 14 | nd |
| | | | | | | | | 2 | 29 | nd |
| 5 | 20 | 5 | 5 | 20 | 20 | 20 | 20 | 1 | 31 | nd |
| | | | | | | | | 2 | 64 | 19 |
| | | | | | | | | 3 | 51 | 25 |
| | | | | | | | | 4 | 36 | 30 |
| 5 | 20 | 5 | 5 | 20 | 20 | 33 | 33 | 1 | 40 | nd |
| | | | | | | | | 2 | 84 | 7 |
| | | | | | | | | 3 | 81 | 10 |
| | | | | | | | | 4 | 77 | 8 |
| 5 | 20 | 5 | 5 | 20 | 25 | 33 | 33 | 1 | 44 | nd |
| | | | | | | | | 2 | 86 | 7 |
| | | | | | | | | 3 | 83 | 10 |
| | | | | | | | | 4 | 77 | 13 |
| 5 | 20 | 5 | 5 | 20 | 25 | 33 | 43 | 1 | 38 | nd |
| | | | | | | | | 2 | 85 | 5 |
| | | | | | | | | 3 | 87 | 6 |
| | | | | | | | | 4 | 89 | 7 |
| 10 | 10 | 5 | 5 | 20 | 25 | 33 | 43 | 3 | 71 | nd |

Figure 3:
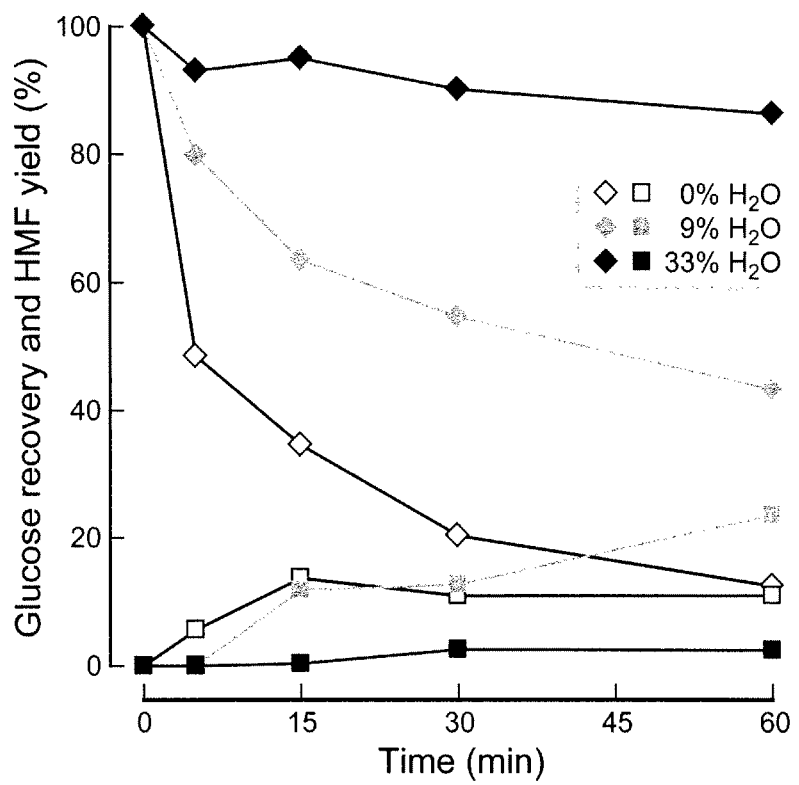
FIG. 3 is a graph showing acid-catalyzed degradation of glucose in [EMIM]Cl. In acidic [EMIM]Cl, glucose (diamonds) disappears rapidly at 100° C., forming HMF (squares) and other degradation products. Increased water content slows glucose loss. Reaction conditions: Glucose, 10 wt %; $H_2SO_4$, 4 wt % relative to glucose.

To examine these alternatives, glucose was reacted in [EMIM]Cl with varying water content (FIG. 3, Table 2). In the results presented, glucose was reacted in [EMIM]Cl at 100° C. with an initial concentration of 10 wt % and a $H_2SO_4$ loading of 4 wt % relative to glucose, except for the first set of entries labeled "a" where no $H_2SO_4$ was added. The water content listed in Table 2 is relative to the total mass of the reaction mixture; glucose recovery is based on HPLC analysis and is normalized to the initial glucose concentration; and HMF molar yield is based on HPLC analysis.

TABLE 2

Acid-catalyzed degradation of glucose in [EMIM]Cl.

| $H_2O$ (wt %) | time (min) | glucose recovery (%) | HMF yield (%) |
|---|---|---|---|
| 0[a] | 0 | 100 | 0 |
| | 5 | 100 | 0 |
| | 15 | 97 | 0 |
| | 30 | 103 | 0 |
| | 60 | 101 | 0 |
| 0 | 0 | 100 | 0 |
| | 5 | 49 | 6 |
| | 15 | 35 | 14 |
| | 30 | 20 | 11 |
| | 60 | 13 | 11 |
| 9 | 0 | 100 | 0 |
| | 5 | 80 | 0 |
| | 15 | 63 | 12 |
| | 30 | 55 | 13 |
| | 60 | 43 | 24 |
| 20 | 0 | 100 | 0 |
| | 5 | 92 | 4 |
| | 15 | 82 | 2 |
| | 30 | 76 | 5 |
| | 60 | 65 | 11 |
| 33 | 0 | 100 | 0 |
| | 5 | 93 | 0 |
| | 15 | 95 | 0 |
| | 30 | 90 | 3 |
| | 60 | 87 | 2 |

In the absence of both acid and water, glucose was recovered unchanged. On the other hand, $H_2SO_4$ caused rapid glucose decay into HMF and other products in ionic liquid with little or no added water. Increasing the water content to 33 wt % decreased the rate of glucose disappearance so that nearly 90% of glucose remained after 1 h. These results suggested that glucose produced by cellulose hydrolysis degrades rapidly under non-aqueous conditions in [EMIM]Cl, but that higher water concentrations prevent glucose loss.

Based on these results, increasing the water concentration in the [EMIM]Cl hydrolysis mixture should enhance glucose yields from cellulose. However, water precipitates cellulose from ionic liquids [27]. For example, a 5 wt % solution of cellulose in [EMIM]Cl formed an intractable gel when the solution was diluted to achieve 10 wt % water, making homogeneous hydrolysis of cellulose in aqueous—ionic liquid solutions impossible. The present disclosure demonstrates that it is possible to balance cellulose solubility and glucose stability by adding water gradually during the hydrolysis. It is believed that cellulose solubility increases as the reaction progresses and that a higher water content can be added after the hydrolysis reaction has progressed without detrimental precipitation of cellulose. For the following experiments, HCl was used as the hydrolysis acid catalyst to match the acid anion (Cl⁻) with that of the ionic liquid. [EMIM]Cl containing 5 wt % cellulose was first treated with HCl and a small amount of water at 105° C. to allow hydrolysis of the cellulose to begin. It is believed that during this initial reaction period, a portion of the cellulose is hydrolyzed into shorter, more soluble segments (Table 1). After a selected time delay, additional water was added to the reaction mixture to stabilize the glucose product. The amount of water added and the timing of additions were varied to assess the effect on glucose yield.

Table 3 provides additional yield results as a function of variation in water addition:

| biomass, (wt %) | HCl (wt %) | water content (wt %) time (min) | | | | | | | | | | time (min) | glucose (%) | xylose (%) |
|---|---|---|---|---|---|---|---|---|---|---|---|---|---|---|
| | | 0' | 3' | 5' | 6' | 10' | 15' | 20' | 25' | 30' | 60' | | | |
| cellulose, 5 | 20 (H$_2$SO$_4$) | 5 | 5 | 5 | 5 | 5 | 5 | 5 | 5 | 5 | 5 | 60 | 40 | |
| cellulose, 5 | 20 | 5 | 5 | 5 | 5 | 5 | 5 | 5 | 5 | 5 | 5 | 60 | 45 | |
| cellulose, 5 | 20 | 5 | 5 | 33 | 33 | 33 | 33 | 33 | 33 | 33 | 33 | 60 | 14 | |
| cellulose, 5 | 20 | 5 | 5 | 5 | 5 | 20 | 20 | 20 | 20 | 20 | 20 | 120 | 29 | |
| | | | | | | | | | | | | 60 | 30 | |
| cellulose, 5 | 20 | 5 | 5 | 5 | 5 | 33 | 33 | 33 | 33 | 33 | 33 | 120 | 68 | |
| | | | | | | | | | | | | 60 | 48 | |
| cellulose, 5 | 20 | 5 | 5 | 5 | 5 | 20 | 20 | 20 | 20 | 33 | 33 | 120 | 31 | |
| | | | | | | | | | | | | 60 | 40 | |
| cellulose, 5 | 20 | 5 | 5 | 5 | 5 | 20 | 20 | 25 | 25 | 33 | 43 | 120 | 85 | |
| | | | | | | | | | | | | 180 | 89 | |
| | | | | | | | | | | | | 60 | 36 | |
| cellulose, 5 | 20 | 5 | 5 | 5 | 5 | 25 | 25 | 33 | 33 | 33 | 33 | 120 | 76 | |
| | | | | | | | | | | | | 180 | 94 | |
| | | | | | | | | | | | | 60 | 33 | |
| cellulose, 5 | 20 | 5 | 5 | 5 | 5 | 20 | 20 | 25 | 25 | 33 | 33 | 120 | 77 | |
| | | | | | | | | | | | | 180 | 62 | |
| | | | | | | | | | | | | 60 | 44 | |
| | | | | | | | | | | | | 120 | 67 | |
| | | | | | | | | | | | | 180 | 81 | |
| cellulose, 5 | 20 | 5 | 5 | 5 | 5 | 20 | 20 | 25 | 25 | 33 | 43 | 120 | 64 | |
| cellulose, 5 | 20 | 5 | 5 | 5 | 5 | 20 | 20 | 25 | 25 | 33 | 43 | 180 | 68 | |
| cellulose, 5 | 20 | 5 | 5 | 5 | 5 | 20 | 20 | 25 | 25 | 33 | 43 | 120 | 58 | |
| cellulose, 5 | 20 | 5 | 5 | 5 | 5 | 20 | 20 | 25 | 25 | 33 | 43 | 180 | 70 | |
| cellulose, 5 | 20 | 5 | 5 | 5 | 20 | 20 | 20 | 20 | 20 | 33 | 43 | 180 | 69 | |
| cellulose, 5 | 20 | 5 | 5 | 5 | 5 | 20 | 20 | 20 | 20 | 33 | 43 | 180 | 70 | |
| cellulose, 10 | 8 | 4 | 4 | 4 | 4 | 20 | 20 | 25 | 25 | 33 | 43 | 210 | 63 | |
| cellulose, 10 | 10 | 3 | 5 | 5 | 10 | 17 | 23 | 23 | 23 | 23 | 23 | 210 | 64 | |
| cellulose, 10 | 10 | 0 | 5 | 5 | 10 | 17 | 23 | 23 | 33 | 33 | 33 | 210 | 67 | |
| cellulose, 10 | 10 | 0 | 5 | 5 | 10 | 17 | 23 | 23 | 33 | 33 | 43 | 210 | 69 | |
| cellulose, 10 | 8 | 0 | 0 | 0 | 0 | 20 | 20 | 25 | 25 | 33 | 43 | 210 | 53 | |
| cellulose, 10 | 3 | 0 | 5 | 5 | 10 | 17 | 23 | 23 | 23 | 33 | 43 | 210 | 30 | |
| cellulose, 10 | 3 | 0 | 0 | 5 | 10 | 17 | 23 | 23 | 33 | 33 | 43 | 210 | 40 | |
| corn stover, 10 stage 1 | 10 | 5 | 5 | 5 | 5 | 20 | 20 | 25 | 25 | 33 | 43 | 60 | 17 | 60 |
| | | | | | | | | | | | | 90 | 21 | 73 |
| | | | | | | | | | | | | 120 | 25 | 80 |
| | | | | | | | | | | | | 150 | 27 | 82 |
| stage 2 | 10 | 5 | 5 | 5 | 5 | 20 | 20 | 25 | 25 | 33 | 43 | 90 | 37 | 5 |
| | | | | | | | | | | | | 120 | 42 | 5 |
| | | | | | | | | | | | | 150 | 44 | 5 |
| | | | | | | | | | | | | 180 | 48 | 5 |
| | | | | | | | | | | | | 210 | 50 | 5 |
| | | | | | | | | | | | | 240 | 54 | 5 |
| corn stover, 10 stage 1 | 10 | 5 | 5 | 5 | 5 | 20 | 20 | 25 | 25 | 33 | 43 | 60 | 17 | 59 |
| | | | | | | | | | | | | 120 | 24 | 78 |
| | | | | | | | | | | | | 150 | 26 | 81 |
| stage 2 | 10 | 5 | 5 | 5 | 5 | 20 | 20 | 25 | 25 | 33 | 43 | 90 | 33 | 4 |
| | | | | | | | | | | | | 120 | 37 | 4 |
| | | | | | | | | | | | | 150 | 39 | 4 |
| | | | | | | | | | | | | 180 | 42 | 4 |
| | | | | | | | | | | | | 210 | 45 | 4 |
| | | | | | | | | | | | | 240 | 49 | 4 |

Note that data in bold in Table 3 is duplicated from other tables herein to facilitate comparison.

The timing of water addition was found to significantly affect glucose yields. For example, when the reaction mixture was diluted to 33% water after 5 min, cellulose precipitated, resulting in low glucose yields. Delaying dilution until after 10 min prevented cellulose precipitation, and gradually increasing the water content to 43% within 60 min provided glucose yields of nearly 90% when hydrolysis was conducted for 2-4 h. The high glucose yields obtained by controlled water addition are nearly twice as high as the previous best yields reported in ionic liquids and approach the glucose yields achieved through enzymatic hydrolysis.

Additionally, varying the amount of time for which cellulose was mixed with the ionic liquid prior to hydrolysis was found to affect yield and by-product formation. Table 4 illustrates this effect. In Table 4, cellulose was reacted in [EMIM]Cl at 105° C. with an initial concentration of 5 wt %; HCl loading is relative to cellulose mass; yields are molar yields based on HPLC analysis and are relative to the glucose monomers contained in the cellulose.

It is believed that increasing the mixing time generally provided improved solvation of the cellulose. However, increasing the mixing time also likely led to increased byproduct formation [36,37] which was indicated by discoloration of the reaction mixture. Thus, for the reaction conditions used, a pre-mixture time of about 6 h was found to provide highest yield. Changes to reaction conditions, e.g., to reaction temperature, cellulose concentration or acid concentration will likely affect the pre-mixing time needed to obtain highest yield. With this optimized pre-mixing procedure, more concentrated cellulose solutions (10 wt %) could be hydrolyzed in high yields.

the acid hydrolysis catalyst (HCl) is buffered by dimethylphosphate or acetate, forming conjugate acids with pKa values of 1.29 and 4.76, respectively [38,39]. The buffered acid is believed to be too weak to accomplish cellulose hydrolysis under the reaction conditions used [33]. In contrast to other ionic liquids, chloride-containing ionic liquids such as [BMIM]Cl, 1-butyl-4-methylpyridinium chloride, and 1-ethylpyridinium chloride both dissolved cellulose and supported hydrolysis with unoptimized glucose yields ranging from 66-73%. These results indicate that the ionic liquid media for cellulose hydrolysis must balance both cellulose solubility and hydrolytic activity. Ionic liquids which are chloride salts are believed to achieve this goal through strong interactions with cellulose coupled with its weak basicity.

TABLE 4

Effect of dissolution time on hydrolysis of cellulose.

| dissolution time (h) | HCl (wt %) | water content (wt %) | | | | | time (h) | glucose yield (%) | HMF yield (%) |
|---|---|---|---|---|---|---|---|---|---|
| | | 0' | 10' | 20' | 30' | 60' | | | |
| 3 | 20 | 5 | 20 | 25 | 33 | 43 | 2 | 86 | 3 |
| | | | | | | | 3 | 90 | 5 |
| | | | | | | | 4 | 92 | 7 |
| 6 | 20 | 5 | 20 | 25 | 33 | 43 | 2 | 89 | 4 |
| | | | | | | | 3 | 93 | 6 |
| | | | | | | | 4 | 92 | 8 |
| 9 | 20 | 5 | 20 | 25 | 33 | 43 | 2 | 83 | 4 |
| | | | | | | | 3 | 86 | 5 |
| | | | | | | | 4 | 87 | 7 |

Figure 4:
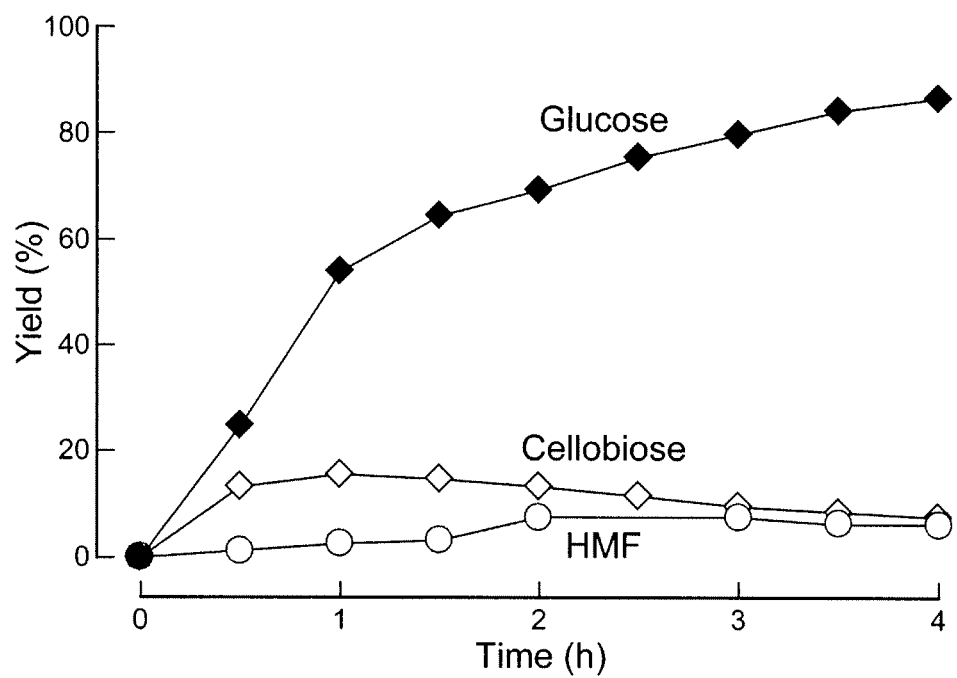
FIG. 4 is a graph showing glucose, HMF, and cellobiose production during cellulose hydrolysis in [EMIM]Cl. Glucose concentrations increase over four hours as cellulose oligomers, such as cellobiose, hydrolyze. Cellulose was reacted under standard optimized reaction conditions.

Tiny cellulose fibers were observed in these reaction mixtures prior to controlled water additions. This observation suggests incomplete cellulose breakdown prior to water addition which could in part explain lower glucose yields. It is believed that cellulose is largely converted into a mixture of glucose and soluble oligomers within about the first 30-60 min of the hydrolysis reaction, and that these oligomers are subsequently hydrolyzed into glucose. Monitoring glucose and cellobiose (a glucose dimer) concentrations during hydrolysis revealed that cellobiose concentrations peaked at 1 h and decayed as glucose concentrations increased (FIG. 4).

Alternative ionic liquids were investigated as solvents for hydrolysis using the reaction conditions optimized with [EMIM]Cl (Table 5). In Table 5, cellulose was reacted in ionic liquid for 3 h at 105° C. after mixing at 105° C. for 6 h; HCl loading was 20 wt % relative to cellulose weight; the water content of the reaction was initially 5 wt % and was increased as follows: 20% (10 min), 25% (20 min), 33% (30 min), 43% (60 min). Yields are molar yields based on HPLC analysis and are relative to the glucose monomers contained in the cellulose. Ionic liquids that did not dissolve cellulose produced poor glucose yields. [EMIM]NO$_3$ and [EMIM]BF$_4$ failed to swell cellulose, and no glucose production was detected with these solvents. The corresponding bromide and triflate salts of [EMIM] did swell cellulose, but resulted in only 4-5% glucose yields. On the other hand, the ionic liquids 1,3-dimethylimidazolium dimethylphosphate and [EMIM]OAc are excellent solvents for cellulose[37]. However, on timed addition of water to 20%, the cellulose in the dimethylphosphate ionic liquid formed a viscous gel, and analysis of the reaction mixture revealed no glucose. Although cellulose remained dissolved in [EMIM]OAc under the reaction conditions, no glucose was produced in this solvent. It is believed that hydrolysis was prevented in these two ionic liquids because

TABLE 5

Hydrolysis of cellulose in Various ionic liquids.

| ionic liquid | cellulose concentration (wt %) | glucose yield (%) |
|---|---|---|
| [EMIM]OAc | 2 | 0 |
| [EMIM]OAc | 5 | 0 |
| [EMIM]NO$_3$ | 2 | 0 |
| 1,3-dimethylimidazolium dimethylphosphate | 2 | 0 |
| 1,3-dimethylimidazolium dimethylphosphate | 5 | 0 |
| [EMIM]Br | 2 | 4 |
| [BMIM]BF$_4$ | 2 | 0 |
| [EMIM]OTf | 2 | 5 |
| [BMIM]Cl | 5 | 66 |
| 1-butyl-4-methylpyridinium chloride | 5 | 73 |
| 1-ethylpyridinium chloride | 5 | 69 |
| 1-ethyl-2,3-dimethylimidazolium chloride | 5 | 46 |

Complex and heterogeneous, lignocellulosic biomass presents a more significant challenge for hydrolysis than does cellulose. In addition to intractable crystalline cellulose, lignocellulosic biomass such as corn stover includes protective hemicellulose and lignin, heterogeneous components that are major obstacles to many biomass hydrolysis processes [3,9]. Nevertheless, chloride ionic liquids are excellent solvents for lignocellulosic biomass.

Figure 5:
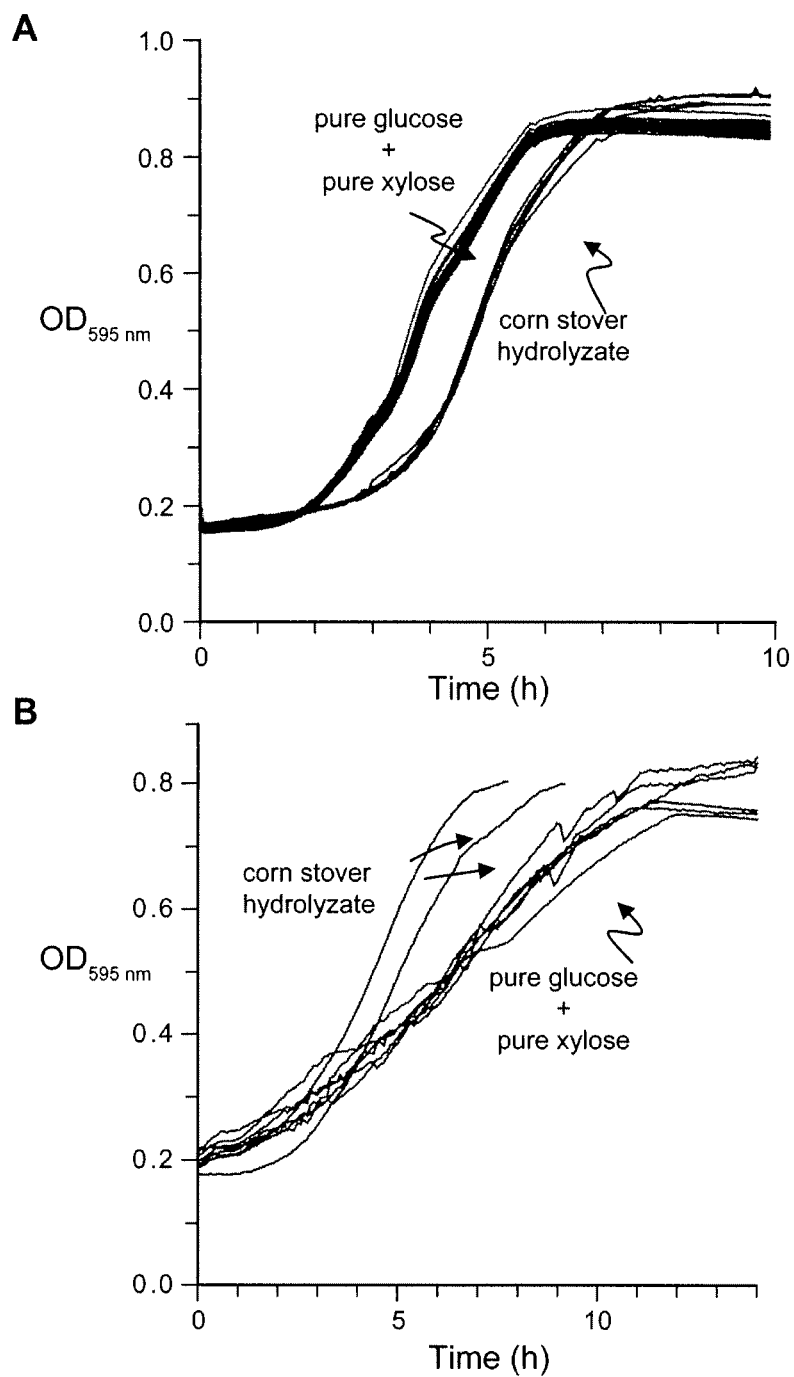
FIG. 5 shows aerobic growth of ethanologenic microbes on corn stover hydrolyzate sugars. The bacterium *Escherichia coli* (A) and yeast *Pichia stipitis* (B) grow rapidly on corn stover hydrolyzate sugars as their sole carbon source. On hydrolyzate, the mean doubling time for *E. coli* was 2.77 h; on pure sugars the doubling time was 2.95 h.

Application of the controlled water addition method and reaction conditions applied to cellulose described herein to hydrolysis of xylan, a hemicellulose, produced xylose in 77% yield. The process for cellulose hydrolysis was then extended to the hydrolysis of corn stover in two stages (Table 6). In a first stage, untreated corn stover that had been mixed with [EMIM]Cl was hydrolyzed with 10 wt % HCl at 105° C. with the same controlled water-dilution process used for pure cellulose. The first stage process produced a 71% yield of xylose and 42% yield of glucose based on the xylan and cellulose content of the stover. Dilution of the reaction mixture of the first stage to 70% water caused precipitation of unhydrolyzed polysaccharides and lignin. These residues were then dissolved in [EMIM]Cl and subjected to an identical second-stage hydrolysis, which released additional xylose and glucose, leaving behind lignin-containing solids. Combined, these two steps resulted in a 79% xylose yield and 70% glucose yield using only simple chemical reagents. The two stage process as described herein is amenable to hydrolysis of other biomass sources, such as wood and grasses. Additional reaction stages can be employed, if desired, to achieve additional yield improvements. Table 3 (above) provides yield results for additional variations of corn stover hydrolysis.

neered KO11 strain produces ethanol selectively [41]. Serving as the sole carbon source, a glucose-xylose-arabinose mixture from corn stover enabled aerobic growth of *E. coli* KO11 at a rate comparable to that of a control glucose-xylose mixture (FIG. 5, graph A). Moreover, under oxygen-deficient conditions, *E. coli* KO11 produced a 79±4% yield of ethanol from stover hydrolyzate sugars and a 76±3% yield from pure xylose and glucose, demonstrating that sugars from our hydrolysis process can be readily converted into ethanol.

Engineered bacteria show promise for biofuel production, but yeast fermentation predominates today [42, 43]. *Pichia stipitis*, which has an innate ability to ferment xylose, is a yeast candidate for bioconversion of lignocellulose-derived sugars [44-46]. Corn stover hydrolyzate sugars are an excellent carbon source for the growth of this yeast (FIG. 5, graph B), and *P. stipitis* efficiently converts hydrolyzate into etha-

TABLE 6

Hydrolysis of corn stover in [EMIM]Cl.

| stover (wt %) | stage | HCl (wt %) | 0' | 5' | 10' | 20' | 30' | 60' | time (h) | glucose yield (%) | xylose yield (%) |
|---|---|---|---|---|---|---|---|---|---|---|---|
| 5 | 1 | 20 | 5 | 5 | 20 | 25 | 33 | 43 | 2.5 | 42 | 71 |
| | 2 | 20 | 5 | 5 | 20 | 25 | 33 | 43 | 3.0 | 28 | 8 |
| | overall | | | | | | | | | 70 | 79 |
| 10 | 1 | 10 | 5 | 5 | 20 | 25 | 33 | 43 | 3.5 | 19 | 74 |
| | 2 | 10 | 5 | 5 | 20 | 25 | 33 | 43 | 3.0 | 47 | 1 |
| | overall | | | | | | | | | 66 | 75 |
| 10 | 1 | 10 | 5 | 5 | 20 | 25 | 33 | 43 | 1.0 | 17 | 60 |
| | 1 | | | | | | | | 1.5 | 21 | 73 |
| | 1 | | | | | | | | 2.0 | 25 | 80 |
| | 1 | | | | | | | | 2.5 | 27 | 82 |
| | 2 | 10 | 5 | 5 | 20 | 25 | 33 | 43 | 1.5 | 37 | 5 |
| | 2 | | | | | | | | 2.0 | 42 | 5 |
| | 2 | | | | | | | | 2.5 | 44 | 5 |
| | 2 | | | | | | | | 3.0 | 48 | 5 |

Corn stover was reacted in [EMIM]Cl at 105° C. after its dissolution at 105° C. for 6 h. HCl loading is relative to stover weight. Yields are molar yields based on HPLC analysis and are relative to the glucose and xylose monomers contained in the stover.

A practical biomass hydrolysis process requires efficient means for sugar and reagent recovery. We found that ion-exclusion chromatography enables separation of the sugars and ionic liquid from the corn stover hydrolysis reaction mixture. In this technique, a mixture containing electrolyte and non-electrolyte solutes is separated by passing it through a charged resin [40]. Charged species, such as the ionic liquid, are excluded from the resin, while non-electrolytes, such as sugars, are retained. Passing the corn stover hydrolyzate through a column of [EMIM]-exchanged Dowex® 50 resin allowed laboratory-scale separation of the ionic liquid solvent from the sugars, with >95% recovery of the ionic liquid, 88% recovery of xylose, and 94% recovery of glucose. These yields were not optimized and may be limited by the small scale of the demonstration separation and may be improved upon scale-up. Notably, very efficient ionic liquid recycling is possible, and the ionic liquid is not chemically incorporated into the biomass residue.

The ability to recycle the expensive ionic liquids is important for the economic viability of the hydrolysis process. To support bioconversion, biomass hydrolyzate sugars must be free of contaminants that inhibit microbial growth and fermentation. We found that sugars derived from corn stover through the process described are excellent feedstocks for bacteria and yeast, particularly an ethanologenic or more generally a solventogenic bacterium and yeast.

Whereas wild-type *Escherichia coli* ferments a range of sugars into a mixture of ethanol and organic acids, the enginol. Fermenting xylose and glucose, the yeasts produced a 70±2% yield of ethanol from hydrolyzate and a 72±1% yield from pure sugars.

Commercial chemicals were of reagent grade or better and were used without further purification. Reactions were performed in glass vessels heated in a temperature-controlled oil bath with magnetic stirring. The term "concentrated under reduced pressure" refers to the removal of water and other volatile materials using a Speed Vac concentrator system. Conductivity was measured with an Extech Instruments ExStik II conductivity meter. NMR spectra were acquired with a Bruker DMX-400 Avance spectrometer (1H, 400 MHz; 13C, 100.6 MHz) at the National Magnetic Resonance Facility at Madison (NMRFAM).

1-Ethyl-3-methylimidazolium chloride (99.5%, [EMIM] Cl) was from Solvent-Innovation (Cologne, Germany). 1-Ethyl-3-methylimidazolium tetrafluoroborate (97%, [EMIM]BF4), 5-hydroxymethylfurfural, birchwood xylan (X0502, 98% xylose residues, ~95% dry solids) and Dowex® 50WX4 (200-400 mesh, H+ form) were from Aldrich (Milwaukee, Wis.). 1-Ethyl-3-methylimidazolium triflate (98.5%, [EMIM]OTf), 1-butyl-3-methylpyridinium chloride (97%, [BMPy]Cl), and 1-ethyl-3-methylimidazolium bromide (97%, [EMIM]Br) were from Fluka (Geel, Belgium). 1-Ethylpyridinium chloride (98%, [EtPy]Cl), 1-ethyl-2,3-dimethylimidazolium chloride (98%, [MMEIM]Cl), and furfural were from Acros (Buchs, Switzerland). Cellulose (medium cotton linters, C6288, ~95% dry solids) was from Sigma (St. Louis, Mo.). Milled and sieved corn stover (~95% dry solids) was obtained from B. E. Dale and coworkers (Michigan State University) [see: Chundawat, S. P. S., Venkatesh, B., & Dale, B. E., Effect of particle size based separation of milled corn stover on AFEX pretreatment and enzymatic digestibility. Biotechnol. Bioeng. 96 (2), 219-231 (2006)], and was passed through a 40-mesh screen prior to use.

Analytical Methods. All reaction products were analyzed by HPLC and quantified with calibration curves generated from commercially available standards. Following a typical reaction, the product mixture was diluted with a known mass of deionized water, subjected to centrifugation or filtration to remove insoluble products, and analyzed. The concentrations of products were calculated from HPLC-peak integrations and used to calculate molar yields. HPLC was performed with an Agilent 1200 system equipped with refractive index and photodiode array detectors as well as a Bio-Rad Aminex HPX-87H column (300×7.8 mm; 5 mM $H_2SO_4$, 0.6 ml/min, 65° C.).

Exemplary Procedure for Hydrolysis of Cellulose. Cellulose (18.7 mg, 104 μmol glucose units) and [EMIM]Cl (380 mg) were mixed at 105° C. for 6 h to form a viscous solution. To this solution was added aqueous HCl (1.66 M, 23.2 μl; equivalent to 3.8 mg concd. HCl), and the reaction mixture was stirred vigorously at 105° C. During this time, the viscosity of the solution decreased dramatically. After 10 min, deionized water (80 μl) was added with stirring, followed by additional aliquots of water at 20 min (40 μl), 30 min (60 μl), and 60 min (100 μl). After a total reaction time of 3 h, the solution was diluted with water (701 μl). Insoluble materials were removed by centrifugation, and the solution was analyzed by HPLC (12.4 mg/g glucose, 88% yield; 0.34 mg/g HMF, 3% yield). In other cases, aliquots of the reaction mixture were removed periodically for HPLC analysis.

Reactions utilizing ionic liquids with melting points >105° C. (e.g., 1-butyl-4-methylpyridinium chloride, 1-ethylpyridinium chloride, and 1-ethyl-2,3-dimethylimidazolium chloride) required slightly different handling. In these cases the ionic liquid and cellulose were heated together using a heat gun until dissolution of the cellulose was achieved. Then, the mixture was heated at 105° C. for 6 h prior to the hydrolysis reaction. Although the 1-ethylpyridinium chloride solution remained liquid at this temperature, the other cellulose solutions solidified. Before addition of HCl, these solids were melted with a heat gun, and they remained liquid after the addition of aqueous HCl.

Representative Reaction of Glucose in [EMIM]Cl. Glucose (47.2 mg, 262 μmol) was dissolved in [EMIN]Cl (460 mg) and deionized water (50 μl). Concd. $H_2SO_4$ (5.5 μl) was added, and the resulting solution was stirred at 100° C. Aliquots of the reaction mixture were removed periodically for HPLC analysis.

Exemplary Hydrolysis of Xylan. Xylan (9.4 mg, 66 μmol xylose units) and [EMIM]Cl (188 mg) were mixed at 105° C. for several hours to form a viscous solution. To this solution was added aqueous HCl (1.66 M, 11 μl), and the reaction mixture was stirred vigorously at 105° C. After 10 min, deionized water (40 μl) was added with stirring, followed by additional aliquots at 20 min (20 μl), 30 min (30 μl), 60 min (50 μl), and 90 min (50 μl). After a total reaction time of 3 h, the solution was diluted with water (100 μl). Insoluble materials were removed by centrifugation, and the solution was analyzed by HPLC (15.3 mg/g xylose, 77% yield).

Representative Procedure for Hydrolysis of Corn Stover. Corn stover (26.7 mg, 54 μmol glucose units, 44 μmol xylose units) and [EMIM]Cl (502 mg) were mixed at 105° C. for 6 h. To this mixture was added aqueous HCl (1.66 M, 29 μl, equivalent to 5 mg concd. HCl), and the reaction mixture was stirred vigorously at 105° C. After 10 min, deionized water (100 μl) was added with stirring, followed by additional aliquots at 20 min (50 μl), 30 min (75 μl), and 60 min (125 μl). After a total reaction time of 2.5 h, the solution was diluted with water (750 μl). Insoluble materials were removed by centrifugation, rinsed twice with water (200 μl), and dried. The liquid products (2.046 g) were analyzed by HPLC (2.0 mg/g glucose, 42% yield; 2.3 mg/g xylose, 71% yield).

The brown solids from the first hydrolysis were then heated with [EMIM]Cl (306 mg) at 105° C. for 4.5 h. To this mixture was added aqueous HCl (1.66 M, 14.5 μl, equivalent to 2.5 mg concd. HCl), and the reaction mixture was vigorously stirred at 105° C. After 10 min, deionized water (50 μl) was added with stirring, followed by an additional 25 μl water at 20 min, 67.5 μl water at 30 min, and 70 μl water at 60 min. After 3 h total reaction time, the solution was diluted with water (300 μl) and centrifuged to sediment insoluble materials. The liquid products (770 mg) were analyzed by HPLC (3.56 mg/g glucose, 28% yield; 0.7 mg/g xylose, 8% yield). For the two-step process, the overall yield of glucose was 70% and the overall yield of xylose was 79%.

In other cases, aliquots of the reaction mixture were removed periodically for HPLC analysis.

Representative Procedure for Recovery of Sugars and [EMIM]Cl from Hydrolysis's. Dowex® 50WX4 (75 g, 0.128 equiv) in a slurry with deionized water was placed in a jacketed column (120 cm×1 cm, Knots #420870-1200) maintained at 65° C., resulting in a resin bed of 0.10 m. The resin was exchanged with [EMIM]+ by passing [EMIM]Cl (64 g, 0.44 mol) in water through the column. At the end of the exchange procedure, the column effluent was neutral, signifying complete exchange of H+ for [EMIM]+. Degassed, deionized water was then passed through the column to elute any solutes.

Hydrolyzate liquids (2.741 g, 8.5 mg glucose, 17.7 mg xylose, ~60% water) were obtained from the hydrolysis reaction of corn stover (102.3 mg) using [EMIM]Cl (1046 mg) under standard conditions. The solid residue from the reaction was reserved for a second hydrolysis reaction. A portion of the first hydrolysis liquids (2.591 g) was loaded on the top of the resin column and eluted with degassed, deionized water at a rate of 3 cm/min. Fractions were collected and analyzed by HPLC (7.5 mg glucose, 94%; 14.3 mg xylose, 86%). The fractions containing [EMIM]Cl were concentrated under reduced pressure, mixed with $D_2O$, and pooled, resulting in a $D_2O$/[EMIM]Cl solution (3.673 g). An aliquot (342.8 mg) of this solution was combined with N,N-dimethylacetamide (71.5 mg, 0.821 mol), and the resulting solution was analyzed by 1H NMR spectroscopy. Integration of the spectra revealed a 0.708:1 molar ratio of [EMIM]Cl:DMA, indicating [EMIM]Cl recovery of 913 mg (92%).

The above process was repeated with the hydrolyzate liquids (1.684 g) from the reaction of the solid residue using [EMIM]Cl (471 mg). After chromatography of a portion of the liquids (1.534 g), the ionic liquid-containing fractions were concentrated under reduced pressure, mixed with D2O, and pooled, resulting in a D2O/[EMIM]Cl solution (3.261 g). An aliquot (528.4 mg) of this solution was combined with N,N-dimethylacetamide (79.6 mg, 0.914 mmol), and the resulting solution was analyzed by 1H NMR spectroscopy. Integration of the spectra revealed a 0.532:1 molar ratio of [EMIM]Cl:DMA, indicating [EMIM]Cl recovery of 440 mg (103%). The combined [EMIM]Cl recovery from the two-step process was 96%.

Sugar-containing fractions from the separation process which were free of [EMIM]Cl were pooled and lyophilized to a brown residue. This residue was dissolved in deionized water (5 mL) and used for microbial growth and fermentation studies, see FIG. 5.

Bacterial Growth Studies. *Escherichia coli* KO11 was a gift from W. D. Marner and coworkers. In all cases *Escherichia coli* were grown at 37° C. in media containing chloramphenicol (40 mg/l). A single colony was inoculated into Luria-Bertani medium [54] (4 ml) containing xylose (0.4 wt %). After incubation in a culture tube agitated at 250 rpm for 18 h, the cells were collected by centrifugation and resuspended in M9 minimal medium [54] (2 ml) free of any carbon source. In a polystyrene 96-well plate, 20 wells were filled with M9 minimal medium (150 µl) containing xylose (2.62 g/l) and glucose (1.38 g/l). Ten wells were filled with M9 minimal medium (150 µl) supplemented with corn stover hydrolyzate sugars (2.62 g/l xylose, 1.38 g/l glucose, and 0.91 g/l arabinose). The remaining wells were filled with deionized water (200 µl). Each well was inoculated with the above cell suspension (5 µl), and the plate was capped with a low-evaporation lid and incubated with rapid agitation in a BioTek ELx808 Absorbance Microplate Reader. The OD595 nm of each well was measured every 5 min for 25 h. Doubling times for each well were calculated from a fit of the OD595 nm values to a modified Gompertz function. [55]

Bacterial Fermentation Studies. To maintain a low-oxygen environment, fermentation with *E. coli* was performed in a glass test tube (13×100 mm) fitted with a rubber stopper, which was pierced with a steel cannula. The other end of the cannula was immersed in water in a second glass test tube. The second test tube was fitted with a rubber stopper pierced with a needle for gas escape.

A single colony was inoculated into LB medium (4 ml) containing xylose (0.26 wt %) and glucose (0.14 wt %). After incubation in a culture tube agitated at 250 rpm for 11 h, the cells were collected by centrifugation and resuspended in fresh LB medium (4 ml). An aliquot (10 µl) of this cell suspension was added to test tubes equipped for anaerobic growth containing LB medium (1.5 ml) supplemented with either xylose (2.62 g/l) and glucose (1.38 g/l), or corn stover hydrolyzate sugars (2.62 g/l xylose, 1.38 g/l glucose, and 0.91 g/arabinose). Each medium was tested in triplicate. Following a purge with $N_2(g)$, fermentation was performed with agitation at 250 rpm. After 12 h, the cultures were analyzed by HPLC for sugars and ethanol. The sugars were consumed completely in all cultures. The ethanol titer was compared to a theoretical yield of 0.51 g ethanol/g sugar (2.04 g/l for pure sugars or 2.25 g/l for corn stover hydrolyzate).

Yeast Growth Studies. *Pichia stipitis* CBS 6054 was a gift from T. W. Jeffries and coworkers. All cultures of *Pichia* were grown at 30° C. A single colony was used to inoculate YP medium (6 ml; 10 g/l yeast extract and 20 g/l peptone) containing xylose (1.2 wt %) and glucose (0.8 wt %). After incubation in a culture tube agitated at 225 rpm for 11 h, the cells in a 1-ml aliquot of the culture were collected by centrifugation. The cells were resuspended in synthetic minimal medium (0.5 ml) containing yeast nitrogen base without amino acids (6.7 g/l; Difco).

In a polystyrene 96-well plate, 10 wells were filled with synthetic minimal medium (150 µl) containing xylose (1.82 g/l), glucose (2.18 g/l), and arabinose (0.33 g/l). Five wells were filled with synthetic minimal medium (150 µl) supplemented with corn stover hydrolyzate sugars (1.82 g/l xylose, 2.18 g/l glucose, and 0.33 g/l arabinose). The remaining wells were filled with deionized water (150 µl). Each well was inoculated with the above cell suspension (10 µl), and the plate was capped with a low-evaporation lid and incubated with rapid agitation in a BioTek ELx808 Absorbance Microplate Reader. The OD595 nm of each well was measured every 5 min for 19 h.

Yeast Fermentation Studies. For fermentation experiments, *P. stipitis* were grown at 30° C. in YP medium (10 g/l yeast extract and 20 g/l peptone) containing the appropriate carbon source. A single colony was inoculated into medium (6 ml) containing 1.2 wt % xylose and 0.8 wt % glucose. After incubation in a culture tube agitated at 225 rpm for 11 h, the yeast suspension was added to glass test tubes containing YP medium (1.5 ml) supplemented with either xylose (3.24 g/l), glucose (3.88 g/l), and arabinose (0.58 g/l), or corn stover hydrolyzate sugars (3.24 g/l xylose, 3.88 g/l glucose, and 0.58 g/l arabinose). The sugar medium was tested in triplicate, and the hydrolyzate medium, in duplicate. The test tubes were fitted with rubber stoppers pierced with needles and agitated at 150 rpm. After 52 h, the cultures were analyzed by HPLC for sugars and ethanol. The sugars were consumed completely in all cultures. The ethanol titer was compared to a theoretical yield of 0.51 g ethanol/g of glucose and xylose (3.63 g/l for pure sugars or 3.63 g/l for corn stover hydrolyzate).

REFERENCES

1. US National Petroleum Council., *Facing the Hard Truths about Energy*. (Washington, D.C., 2007).
2. Smeets, E. M. W., Faaij, A. P. C., Lewandowski, I. M., & Turkenburg, W. C., A bottom-up assessment and review of global bio-energy potentials 2050. *Prog. Energy Combust. Sci.* 33, 56-106 (2007).
3. Dumitriu, S. ed., Polysaccharides: Structural Diversity and Functional Versatility, 2nd ed. (Marcel Dekker, New York, 2005).
4. Peters, D., Raw materials. *Adv. Biochem. Eng./Biotechnol.* 105, 1-30 (2007).
5. Lange, J.-P., Lignocellulose conversion: An introduction to chemistry, process and economics. *Biofuels Bioprod. Bioref.* 1, 39-48 (2007).
6. Chheda, J. N., Huber, G. W., & Dumesic, J. A., Liquid-phase catalytic processing of biomass-derived oxygenated hydrocarbons to fuels and chemicals. *Angew. Chem. Int. Ed.* 46, 7164-7183 (2007).
7. Van Haveren, J., Scott, E. L., & Sanders, J., Bulk chemicals from biomass. *Biofuels Bioprod. Bioref.* 2, 41-57 (2008).
8. Christensen, C. H., Rass-Hansen, J., Marsden, C. C., Taarning, E., & Egeblad, K., The renewable chemicals industry. *ChemSusChem* 1, 283-289 (2008).
9. Himmel, M. E. et al., Biomass recalcitrance: Engineering plants and enzymes for biofuels production. *Science* 315, 804-807 (2007).
10. Mosier, N. et al., Features of promising technologies for pretreatment of lignocellulosic biomass. *Bioresour. Technol.* 96, 673-686 (2005).
11. Wyman, C. E. et al., Comparative sugar recovery data from laboratory scale application of leading pretreatment technologies to corn stover. *Bioresour. Technol.* 96, 2026-2032 (2005).
12. Aden, A. et al. Lignocellulosic Biomass to Ethanol Process Design and Economics Utilizing Co-Current Dilute Acid Prehydrolysis and Enzymatic Hydrolysis for Corn Stover, edited by DOE (National Renewable Energy Laboratory, Golden, Colo., 2002).
13. Braconnot, H., Sur la conversion du corps ligneux en gomme, en sucre, et en un acide d'une nature particuliere, 13. par le moyen de l'acide sulfurique; conversion de la même substance ligneuse en ulmine par la potasse. *Ann. Chim. Phys.* 12, 172-195 (1819).
14. Stern, A. L., X. Contributions to the chemistry of cellulose. I. Celluose-sulphuric acid, and the products of its hydrolysis. *J. Chem. Soc., Trans.*, 74-90 (1895).
15. Xiang, Q., Lee, Y. Y., Pettersson, P. O., & Torget, R. W., Heterogeneous aspects of acid hydrolysis of α-cellulose. *Appl. Biochem. Biotechnol.* 105, 505-514 (2003).
16. Bergius, F., Conversion of wood to carbohydrates. *Ind. Eng. Chem.* 29, 247-253 (1937).
17. Schoenemann, K., The perfecting of wood hydrolysis in the Rheinau process. *Chim. Ind. (Paris)* 80, 140-150 (1958).
18. Dunning, J. W. & Lathrop, E. C., The saccharification of agricultural residues: A continuous process. *Ind. Eng. Chem.* 37, 24-29 (1945).
19. Tsao, G. T., Ladisch, M. R., Voloch, M., & Bienkowski, P. R., Production of ethanol and chemicals from cellulosic materials. *Process Biochem.,* 34-38 (1982).
20. Wright, J. D. & D'Agincourt, C. G. Evaluation of sulfuric acid hydrolysis processes for alcohol fuel production, edited by DOE (Solar Energy Research Institute, Golden, Colo., 1984).
21. Wright, J. D. & Power, A. J., Comparative technical evaluation of acid hydrolysis processes for conversion of cellulose to alcohol in *Energy from Biomass and Wastes* (Institute of Gas Technology, Chicago, 1987), Vol. 10, pp. 949-971.
22. Farina, G. E., Barrier, J. W., & Forsythe, M. L., Fuel alcohol production from agricultural lignocellulosic feedstocks. *Energy Sources* 10, 231-237 (1988).
23. Farone, W. A. & Cuzens, J. E., U.S. Pat. No. 5,726,046 (1998).
24. Hermanutz, F., Meister, F., & Uerdingen, E., New developments in the manufacture of cellulose fibers with ionic liquids. *Chem. Fibers Int.* 6, 342-343 (2006).
25. Zhu, S. et al., Dissolution of cellulose with ionic liquids and its application: A mini-review. *Green Chem.* 8, 325-327 (2006).
26. El Seoud, O. A., Koschella, A., Fidale, L. C., Dorn, S., & Heinse, T., Applications of ionic liquids in carbohydrate chemistry: A window of opportunities. *Biomacromolecules* 8, 2629-2647 (2007).
27. Swatloski, R. P., Spear, S. K., Holbrey, J. D., & Rogers, R. D., Dissolution of cellose with ionic liquids. *J. Am. Chem. Soc.* 124, 4974-4975 (2002).
28. Li, C. & Zhao, Z. K., Efficient acid-catalyzed hydrolysis of cellulose in ionic liquid. *Adv. Synth. Catal.* 349, 1847-1850 (2007).
29. Li, C., Wang, Q., & Zhao, Z. K., Acid in ionic liquid: An efficient system for hydrolysis of lignocellulose. *Green Chem.* 10, 177-182 (2008).
30. Rinaldi, R., Palkovits, R., & Schüth, F., Depolymerization of cellulose using solid catalysts in ionic liquids. *Angew. Chem. Int. Ed.* 47, 8047-8050 (2008).
31. Sievers, C. et al., Ionic-liquid-phase hydrolysis of pine wood. *Ind. Eng. Chem. Res.* 48, 1277-1286 (2009).
32. Fanselow, M., Holbrey, J. D., & Seddon, K. R., Eur. Patent Application Patent No. 1860201 (2007).
33. Vanoye, L., Fanselow, M., Holbrey, J. D., Atkins, M. P., & Seddon, K. R., Kinetic model for the hydrolysis of lignocellulosic biomass in the ionic liquid, 1-ethyl-3-methyl-imidazolium chloride. *Green Chem.* 11, 390-396 (2009).
34. Cao, N. J., Xu, Q., & Chen, L. F., Acid hydrolysis of cellulose in zinc chloride solution. *Appl. Biochem. Biotechnol.* 51, 21-28 (1995).
35. Rivers, D. B., Gracheck, S. J., Woodford, L. C., & Emert, G. H., Limitations of the DNS assay for reducing sugars from saccharified lignocellulosics. *Biotechnol. Bioeng.* 26, 800-802 (1984).
36. Ebner, G., Schiehser, S., Potthast, A., & Rosenau, T., Side reaction of cellulose with common 1-alkyl-3-methylimidazolium-based ionic liquids. *Tetrahedron Lett.* 49, 7322-7324 (2008).
37. Vitz, J., Erdmenger, T., Haensch, C., & Schubert, U. S., Extended dissolution studies of cellulose in imidazolium based ionic liquids. *Green Chem.* 11, 417-424 (2009).
38. Kumler, W. D. & Eiler, J. J., The acid strength of mono and diesters of phosphoric acid. The n-alkyl esters from methyl to butyl, the esters of biological importance, and the natural guanidine phosphoric acids. *J. Am. Chem. Soc.* 65, 2355-2361 (1943).
39. Dippy, J. F. J., Hughes, S. R. C., & Rozanski, A., Chemical constitution and the dissociation constants of manocarboxylic acids. Part XVIII. Some acetic and propionic acids substituted with hydrocarbon radicals in 10% and 25% (w/w) acetone-water solutions. *J. Chem. Soc.,* 1441-1446 (1959).
40. Asher, D. R., Sugar purification by ion exclusion. *Ind. Eng. Chem.* 48, 1465-1466 (1956).
41. Dien, B. S., Cotta, M. A., & Jeffries, T. W., Bacteria engineered for fuel ethanol production: current status. *Appl. Microbiol. Biotechnol.* 63, 258-266 (2003).
42. Ho, N. W. Y., Chen, Z., Brainard, A. P., & Sedlak, M., Successful design and development of genetically engineered *Saccharomyces* yeasts for effective cofermentation of glucose and xylose from cellulosic biomass to fuel ethanol. *Adv. Biochem. Eng./Biotechnol.* 65, 163-192 (1999).
43. Van Maris, A. J. A. et al., Development of efficient xylose fermentation in *Saccharomyces cerevisiae*: Xylose isomerase as a key component. *Adv. Biochem. Eng./Biotechnol.* 108, 179-204 (2007).
44. Jeffries, T. W., Emerging technology for fermenting D-xylose. *Trends Biotechnol.* 3, 208-212 (1985).
45. Agbogbo, F. K., Haagensen, F. D., Milam, D., & Wenger, K. S., Fermentation of acid-pretreated corn stover to ethanol without detoxification using *Pichia stipitis*. *Appl. Biochem. Biotechnol.* 145, 53-58 (2008).
46. Agbogbo, F. K. & Coward-Kelly, G., Cellulosic ethanol production using the naturally occurring xylose-Fermenting yeast, pichia stipitis. *Biotechnol. Lett* 30, 1515-1524 (2008).
47. Maeda, T., Sanchez-Torres, V., & Wood, T. K., Enhanced hydrogen production from glucose by metabolically engineered *Escherichia coli*. *Appl. Microbiol. Biotechnol.* 77, 879-890 (2007).
48. Atsumi, S., Hanai, T., & Liao, J. C., Non-fermentative pathways for synthesis of branched-chain higher alcohols as biofuels. *Nature* 451, 86-89 (2008).
49. Fortman, J. et al., Biofuel alternatives to ethanol: Pumping the microbial well. *Trends Biotechnol.* 26, 375-381 (2008).
50. Kunkes, E. L. et al., Catalytic conversion of biomass to monofunctional hydrocarbons and targeted liquid-fuel classes. *Science* 322, 417-421 (2008).
51. Binder, J. B. & Raines, R. T., Simple chemical transformation of lignocellulosic biomass into furans for fuels and chemicals. *J. Am. Chem. Soc.* 131, 1979-1985 (2009).
52. Lora, J. H. & Glasser, W. G., Recent industrial applications of lignin: A sustainable alternative to nonrenewable materials. *J. Polym. Environ.* 10, 39-48 (2002).
53. Zhao, H., Holladay, J. E., Brown, H., and Zhang, Z. C., Metal Chlorides in Ionic Liquids Convert Sugars to 5-Hydroxymethylfurfural, Science 316:1597-1600 (2007)

54. Sambrook, J. & Russell, D. W., Molecular Cloning: A Laboratory Manual, 3rd ed. (Cold Spring Harbor Laboratory Press, Cold Spring Harbor, N.Y.) (2001)
55. Zwietering, M. H., Jongenburger, I., Rombouts, F. M., & van't Riet, K., Modeling of the bacterial growth curve. Appl. Environ. Microbiol. 56, 1875-1881 (1990)
56. Mosier, N., et al., featured of promising technologies for pretreatment of lignocellulosic biomass, Bioresource Technol. 96:673-686 (2005)

We claim:

1. A method for hydrolyzing a biomass polysaccharide substrate comprising hydrolyzing a reaction mixture comprising the biomass polysaccharide substrate, acid and an ionic liquid in which cellulose is soluble and adding water to the reaction mixture, wherein water is added at a rate such that the polysaccharide of the biomass polysaccharide substrate is not precipitated from the reaction mixture and hydrolysis is not substantially inhibited, wherein the biomass polysaccharide substrate is lignocellulosic biomass, wherein hydrolysis is continued until the monosaccharide yield is 50% or higher, and wherein water is added until the total amount of water is at least 20 weight % of the reaction mixture.

2. The method of claim 1 wherein the amount of acid ranges from about 5 weight % to 40 weight % relative to the amount of biomass polysaccharide substrate in the reaction.

3. The method of claim 1 wherein the amount of acid ranges from about 10 weight % to 25 weight % relative to the amount of biomass polysaccharide substrate in the reaction.

4. The method of claim 1 wherein the reaction mixture is heated to a temperature of about 70 to 140° C.

5. The method of claim 1 wherein the ionic liquid comprises chloride, trifluoroacetate, trichloroacetate, tribromoacetate or thiocyanate.

6. The method of claim 1 wherein the cation of the ionic liquid is an imidazolium or a pyridinium.

7. The method of claim 1 wherein the ionic liquid is [EMIM]Cl, [BMIM]Cl, 1-ethyl-2,3-dimentylimidazolium chloride or 1-alkylpyridinium chloride.

8. A method for making a monosaccharide feedstock which comprises preparing a hydrolysis product as in claim 1 and separating the hydrolysis product from ionic liquid.

9. The method of claim 6 wherein the anion of the ionic liquid is chloride.

10. A method for hydrolyzing a biomass polysaccharide substrate comprising hydrolyzing a reaction mixture comprising the biomass polysaccharide substrate, acid and an ionic liquid in which cellulose is soluble and adding water to the reaction mixture, wherein water is added at a rate such that the polysaccharide of the biomass polysaccharide substrate is not precipitated from the reaction mixture and hydrolysis is not substantially inhibited, wherein the biomass polysaccharide substrate is lignocellulosic biomass, wherein hydrolysis is continued until the monosaccharide yield is 50% or higher, and wherein:
a) a total water level of 20 weight % with respect to the total reaction mixture is added by 3-10 minutes after initiation of hydrolysis;
b) a total water level of 20 weight % with respect to the total reaction mixture is added by 10 minutes after initiation of hydrolysis;
c) a total water level of 20-35 weight % with respect to the total reaction mixture is added within 10-30 minutes after initiation of hydrolysis;
d) a total water level of 35-45 weight % with respect to the total reaction mixture is added within 30-60 minutes after initiation of hydrolysis; or
e) a total water level of 40-45 weight % with respect to the total reaction mixture is added within 60 minutes after initiation of hydrolysis.

11. A method for making a monosaccharide feedstock which comprises preparing a hydrolysis product as in claim 10 and separating the hydrolysis product from ionic liquid.

12. A method for hydrolyzing a biomass polysaccharide substrate comprising hydrolyzing a reaction mixture comprising the biomass polysaccharide substrate, acid and an ionic liquid in which cellulose is soluble and adding water to the reaction mixture, wherein water is added at a rate such that the polysaccharide of the biomass polysaccharide substrate is not precipitated from the reaction mixture and hydrolysis is not substantially inhibited, wherein the biomass polysaccharide substrate is lignocellulosic biomass, wherein hydrolysis is continued until the monosaccharide yield is 50% or higher, and wherein water is added to the reaction to achieve a total water content of 20 weight % by 10 min. after reaction initiation and additional water is added to achieve a total water content of 40-45 weight % by 60 min. after reaction initiation.

13. The method of claim 12 wherein the ionic liquid is [EMIM]Cl or [BMIM]Cl.

14. The method of claim 13 wherein the concentration of biomass polysaccharide substrate in the initial reaction mixture ranges from 5-10 weight %.

15. The method of claim 14 wherein acid is present in an amount between 10-25 weight % with respect to the amount of biomass polysaccharide substrate.

16. The method of claim 12 wherein the ionic liquid is [EMIM]Cl, [BMIM]Cl, 1-ethyl-2,3-dimentylimidazolium chloride or 1-alkylpyridinium chloride.

17. A method for making a monosaccharide feedstock which comprises preparing a hydrolysis product as in claim 12 and separating the hydrolysis product from ionic liquid.

* * * * *